US010507240B2

(12) United States Patent
Yoon et al.

(10) Patent No.: US 10,507,240 B2
(45) Date of Patent: Dec. 17, 2019

(54) EPITOPE OF HEPATITIS B VIRUS SURFACE ANTIGEN AND BINDING MOLECULE SPECIFICALLY BINDING TO SAME FOR NEUTRALIZING HEPATITIS B VIRUS

(71) Applicant: CELLTRION INC., Incheon (KR)

(72) Inventors: Joon Sun Yoon, Incheon (KR); Hwa Jin Lee, Ulsan (KR); Kye Sook Yi, Incheon (KR); Cheol Min Kim, Bucheon-si (KR); Byung Pil Lim, Seoul (KR); Shin Jae Chang, Incheon (KR); Seung Suh Hong, Seoul (KR)

(73) Assignee: CELLTRION, Inc., Incheon (KR)

( * ) Notice: Subject to any disclaimer, the term of this patent is extended or adjusted under 35 U.S.C. 154(b) by 0 days.

(21) Appl. No.: 15/529,828

(22) PCT Filed: Nov. 27, 2015

(86) PCT No.: PCT/KR2015/012820
§ 371 (c)(1),
(2) Date: May 25, 2017

(87) PCT Pub. No.: WO2016/085284
PCT Pub. Date: Jun. 2, 2016

(65) Prior Publication Data
US 2017/0326231 A1   Nov. 16, 2017

(30) Foreign Application Priority Data
Nov. 28, 2014   (KR) ........................ 10-2014-0167937

(51) Int. Cl.
| | |
|---|---|
| *C07K 16/08* | (2006.01) |
| *A61K 39/12* | (2006.01) |
| *A61K 39/29* | (2006.01) |
| *A61K 39/395* | (2006.01) |
| *C07K 14/02* | (2006.01) |
| *A61K 38/16* | (2006.01) |
| *C12N 15/11* | (2006.01) |
| *C12N 15/63* | (2006.01) |

(52) U.S. Cl.
CPC .......... *A61K 39/292* (2013.01); *A61K 38/162* (2013.01); *A61K 39/29* (2013.01); *A61K 39/395* (2013.01); *C07K 14/02* (2013.01); *C07K 16/08* (2013.01); *C07K 16/082* (2013.01); *C07K 2317/34* (2013.01); *C07K 2317/76* (2013.01); *C07K 2317/92* (2013.01); *C12N 15/11* (2013.01); *C12N 15/63* (2013.01); *C12N 2710/24261* (2013.01)

(58) Field of Classification Search
None
See application file for complete search history.

(56) References Cited

U.S. PATENT DOCUMENTS

| | | | |
|---|---|---|---|
| 7,067,247 B2 | 6/2006 | Zheng | |
| 2011/0033838 A1 | 2/2011 | Bussfeld et al. | |

FOREIGN PATENT DOCUMENTS

| | | |
|---|---|---|
| KR | 10-1281098 B1 | 7/2013 |
| WO | WO 02/019986 A1 | 3/2002 |
| WO | WO 2012/109404 A1 | 8/2012 |
| WO | WO 2013/185558 A1 | 12/2013 |
| WO | WO 2014/193122 A1 | 12/2014 |

OTHER PUBLICATIONS

WO 2014/193122 Machine Translation into English from PatentScope (WIPO). (Year: 2014).*
Partial Supplementary European Search Report dated Nov. 3, 2017 be the European Patent Office in connection with related European Patent Application No. EP 15864087.0.
Milich, et al., "T- and B-cell recognition of hepatitis B viral antigens", Immunol Today, 1988.
Yibin Zhu, et al., "Toward the development of monoclonal antibody-based assays to probe virion-like epitopes in hepatitis B vaccine antigen", Human Vaccines and Immunotherapeutics, 2014.
Anne Marie Roque-Afonso, et al., "Viral and clinical factors associated with surface gene variants among hepatitis B virus carriers," Antiviral Therapy, 2007.
William F. Carman, et al., "The Prevalence of Surface Antigen Variants of Hepatitis B Virus in Papua New Guinea, South Africa, and Sardinia," Hepatology, 1997.
Jessica Salisse, et al., "A Function Essential to Viral Entry Underlies the Hepatitis B Virus "a" Determinant," Journal of Virology, 2009.
International Search Report in connection with PCT International Application No. PCT/KR2015/012820, including English language translation.

* cited by examiner

*Primary Examiner* — Stacy B Chen
(74) *Attorney, Agent, or Firm* — John P. White; Cooper & Dunham LLP

(57) ABSTRACT

The present invention relates to an epitope specific to hepatitis B virus surface antigen and a binding molecule binding to the same for neutralizing hepatitis B virus. Since the epitope provided by the present invention is produced by forming a three-dimensional structure and does not comprise a determinant, by which escape mutation is induced against an administration of existing vaccines or HBIg, a composition comprising an antibody biding to the epitope or a vaccine composition comprising the epitope has a very low possibility of causing a decrease in efficacy due to escape mutation. Therefore, such an antibody or vaccine composition can be very effectively used in prevention and/or treatment of HBV.

Figure 1:
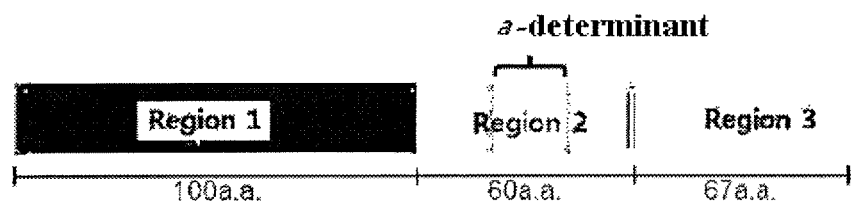

3 Claims, 15 Drawing Sheets
Specification includes a Sequence Listing.

SEQUENCE LISTING

```
<160> NUMBER OF SEQ ID NOS: 24

<210> SEQ ID NO 1
<211> LENGTH: 226
<212> TYPE: PRT
<213> ORGANISM: Artificial Sequence
<220> FEATURE:
<223> OTHER INFORMATION: HBsAg

<400> SEQUENCE: 1

Met Glu Ser Thr Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ala Pro Thr Cys
        35                  40                  45

Pro Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Leu Pro Gly
            100                 105                 110
```

```
                Thr Ser Thr Thr Ser Thr Gly Pro Cys Lys Thr Cys Thr Ile Pro Ala
                            115                 120                 125

Gln Gly Thr Ser Met Phe Pro Ser Cys Cys Thr Lys Pro Ser Asp
                    130                 135                 140

Gly Asn Cys Thr Cys Ile Pro Ile Pro Ser Ser Trp Ala Phe Ala Arg
                145                 150                 155                 160

Phe Leu Trp Glu Trp Ala Ser Val Arg Phe Ser Trp Leu Ser Leu Leu
                                165                 170                 175

Val Pro Phe Val Gln Trp Phe Ala Gly Leu Ser Pro Thr Val Trp Leu
                            180                 185                 190

Ser Val Ile Trp Met Met Trp Tyr Trp Gly Pro Ser Leu Tyr Asn Ile
                            195                 200                 205

Leu Ser Pro Phe Leu Pro Leu Leu Pro Ile Phe Phe Cys Leu Trp Val
                            210                 215                 220

Tyr Ile
                225

<210> SEQ ID NO 2
<211> LENGTH: 21
<212> TYPE: DNA
<213> ORGANISM: Artificial Sequence
<220> FEATURE:
<223> OTHER INFORMATION: Forward primer of realtime-PCR for HBV DNA
      quantitation

<400> SEQUENCE: 2
cacatcagga ttcctaggac c                                             21

<210> SEQ ID NO 3
<211> LENGTH: 20
<212> TYPE: DNA
<213> ORGANISM: Artificial Sequence
<220> FEATURE:
<223> OTHER INFORMATION: Reverse primer of realtime-PCR for HBV DNA
      quantitation

<400> SEQUENCE: 3
aggttggtga gtgattggag                                               20

<210> SEQ ID NO 4
<211> LENGTH: 26
<212> TYPE: DNA
<213> ORGANISM: Artificial Sequence
<220> FEATURE:
<223> OTHER INFORMATION: TaqMan probe of realtime-PCR for HBV DNA
      quantitation

<400> SEQUENCE: 4
cagagtctag actcgtggtg gacttc                                        26

<210> SEQ ID NO 5
<211> LENGTH: 13
<212> TYPE: PRT
<213> ORGANISM: Artificial Sequence
<220> FEATURE:
<223> OTHER INFORMATION: #40 light chain CDR1

<400> SEQUENCE: 5

Ser Gly Ser Ser Ser Asn Ile Gly Lys Asn Ser Val Asn
1               5                   10
```

-continued

```
<210> SEQ ID NO 6
<211> LENGTH: 7
<212> TYPE: PRT
<213> ORGANISM: Artificial Sequence
<220> FEATURE:
<223> OTHER INFORMATION: #40 light chain CDR2

<400> SEQUENCE: 6

Ser Asn Ser Gln Arg Thr Ser
1               5

<210> SEQ ID NO 7
<211> LENGTH: 11
<212> TYPE: PRT
<213> ORGANISM: Artificial Sequence
<220> FEATURE:
<223> OTHER INFORMATION: #40 light chain CDR3

<400> SEQUENCE: 7

Ala Ala Trp Asp Asp Asn Leu Ser Trp Glu Ile
1               5                   10

<210> SEQ ID NO 8
<211> LENGTH: 5
<212> TYPE: PRT
<213> ORGANISM: Artificial Sequence
<220> FEATURE:
<223> OTHER INFORMATION: #40 heavy chain CDR1

<400> SEQUENCE: 8

Ala Ser Tyr Met Gly
1               5

<210> SEQ ID NO 9
<211> LENGTH: 16
<212> TYPE: PRT
<213> ORGANISM: Artificial Sequence
<220> FEATURE:
<223> OTHER INFORMATION: #40 heavy chain CDR2

<400> SEQUENCE: 9

Leu Ile Phe Thr Ala Gly Asn Thr Tyr Tyr Ala Asp Ser Val Arg Gly
1               5                   10                  15

<210> SEQ ID NO 10
<211> LENGTH: 18
<212> TYPE: PRT
<213> ORGANISM: Artificial Sequence
<220> FEATURE:
<223> OTHER INFORMATION: #40 heavy chain CDR3

<400> SEQUENCE: 10

Leu Asn Trp Ala Gly Tyr Ala Tyr Gly Pro Ala Tyr Tyr Tyr Gly Leu
1               5                   10                  15

Asp Val

<210> SEQ ID NO 11
<211> LENGTH: 16
<212> TYPE: PRT
<213> ORGANISM: Artificial Sequence
<220> FEATURE:
<223> OTHER INFORMATION: #4 light chain CDR1

<400> SEQUENCE: 11

Arg Ser Ser Gln Ser Leu Leu His Ser Lys Gly Tyr Asn Tyr Val Asp
1               5                   10                  15
```

```
<210> SEQ ID NO 12
<211> LENGTH: 7
<212> TYPE: PRT
<213> ORGANISM: Artificial Sequence
<220> FEATURE:
<223> OTHER INFORMATION: #4 light chain CDR2

<400> SEQUENCE: 12

Leu Gly Ser Asp Arg Ala Ser
1               5

<210> SEQ ID NO 13
<211> LENGTH: 9
<212> TYPE: PRT
<213> ORGANISM: Artificial Sequence
<220> FEATURE:
<223> OTHER INFORMATION: #4 light chain CDR3

<400> SEQUENCE: 13

Met Gln Ala Leu Gln Ser Pro Pro Val
1               5

<210> SEQ ID NO 14
<211> LENGTH: 5
<212> TYPE: PRT
<213> ORGANISM: Artificial Sequence
<220> FEATURE:
<223> OTHER INFORMATION: #4 heavy chain CDR1

<400> SEQUENCE: 14

Phe Tyr Tyr Trp Ser
1               5

<210> SEQ ID NO 15
<211> LENGTH: 16
<212> TYPE: PRT
<213> ORGANISM: Artificial Sequence
<220> FEATURE:
<223> OTHER INFORMATION: #4 heavy chain CDR2

<400> SEQUENCE: 15

Tyr Val Tyr Ile Ser Gly Asp Thr Asp Tyr Asn Pro Ser Leu Lys Ser
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: #4 heavy chain CDR3

<400> SEQUENCE: 16

Gly His Tyr Gly Ser Gly Ser Asp Tyr Ala Val Tyr Tyr Phe Asp Arg
1               5                   10                  15

<210> SEQ ID NO 17
<211> LENGTH: 111
<212> TYPE: PRT
<213> ORGANISM: Artificial Sequence
<220> FEATURE:
<223> OTHER INFORMATION: #40 light chain variable region

<400> SEQUENCE: 17

Gln Ser Gln Leu Thr Gln Pro Pro Ser Ala Ser Gly Thr Ala Gly Gln
1               5                   10                  15

Arg Val Thr Ile Ser Cys Ser Gly Ser Ser Ser Asn Ile Gly Lys Asn
            20                  25                  30
```

```
Ser Val Asn Trp Tyr Arg Gln Phe Pro Gly Thr Ala Pro Lys Leu Leu
         35                  40                  45

Ile Ser Ser Asn Ser Gln Arg Thr Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Asp Asp Glu Ala Asp Tyr Tyr Cys Ala Ala Trp Asp Asp Asn Leu
                 85                  90                  95

Ser Trp Glu Ile Phe Gly Gly Gly Thr Lys Leu Thr Val Leu Gly
                100                 105                 110

<210> SEQ ID NO 18
<211> LENGTH: 126
<212> TYPE: PRT
<213> ORGANISM: Artificial Sequence
<220> FEATURE:
<223> OTHER INFORMATION: #40 heavy chain variable region

<400> SEQUENCE: 18

Glu Val Gln Leu Val Gln Ser Ala Gly Gly Leu Val Gln Pro Gly Gly
 1               5                  10                  15

Ser Leu Arg Ile Ser Cys Ala Pro Ser Gly Phe Ser Val Arg Ala Ser
             20                  25                  30

Tyr Met Gly Trp Ile Arg Gln Ala Pro Gly Lys Gly Leu Glu Trp Ile
         35                  40                  45

Ser Leu Ile Phe Thr Ala Gly Asn Thr Tyr Tyr Ala Asp Ser Val Arg
 50                  55                  60

Gly Arg Phe Thr Val Ser Arg Asp Ser Ser Arg Asn Thr Leu Tyr Phe
 65                  70                  75                  80

Gln Met Asn Asn Leu Arg Val Gly Asp Thr Ala Val Tyr Tyr Cys Ala
                 85                  90                  95

Arg Leu Asn Trp Ala Gly Tyr Ala Tyr Gly Pro Ala Tyr Tyr Tyr Gly
                100                 105                 110

Leu Asp Val Trp Gly Gln Gly Thr Thr Val Ile Val Ser Ser
            115                 120                 125

<210> SEQ ID NO 19
<211> LENGTH: 112
<212> TYPE: PRT
<213> ORGANISM: Artificial Sequence
<220> FEATURE:
<223> OTHER INFORMATION: #4 light chain variable region

<400> SEQUENCE: 19

Asp Ile Val Met Thr Gln Ser Pro Leu Ser Leu Ser Val Ala Pro Gly
 1               5                  10                  15

Glu Pro Ala Ser Ile Ser Cys Arg Ser Ser Gln Ser Leu Leu His Ser
             20                  25                  30

Lys Gly Tyr Asn Tyr Val Asp Trp Tyr Leu Gln Lys Pro Gly Gln Ser
         35                  40                  45

Pro Gln Leu Leu Ile Tyr Leu Gly Ser Asp Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Ser Pro Pro Val Phe Gly Gly Gly Thr Lys Val Glu Ile Lys
                100                 105                 110
```

```
<210> SEQ ID NO 20
<211> LENGTH: 124
<212> TYPE: PRT
<213> ORGANISM: Artificial Sequence
<220> FEATURE:
<223> OTHER INFORMATION: #4 heavy chain variable region

<400> SEQUENCE: 20

Gln Val Gln Leu Gln Glu Ser Gly Pro Gly Leu Val Arg Pro Ser Glu
1               5                   10                  15

Thr Leu Ser Leu Thr Cys Thr Ile Ser Gly Ser Ile Ser Phe Tyr
            20                  25                  30

Tyr Trp Ser Trp Ile Arg Gln Pro Pro Gly Lys Gly Leu Glu Trp Ile
        35                  40                  45

Gly Tyr Val Tyr Ile Ser Gly Asp Thr Asp Tyr Asn Pro Ser Leu Lys
    50                  55                  60

Ser Arg Val Thr Ile Ser Val Asp Lys Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Arg Gly His Tyr Gly Ser Gly Ser Asp Tyr Ala Val Tyr Tyr Phe Asp
            100                 105                 110

Arg Trp Gly Gln Gly Ala Leu Val Thr Val Ser Ser
        115                 120

<210> SEQ ID NO 21
<211> LENGTH: 235
<212> TYPE: PRT
<213> ORGANISM: Artificial Sequence
<220> FEATURE:
<223> OTHER INFORMATION: #40 light chain

<400> SEQUENCE: 21

Met Ala Ser Phe Pro Leu Leu Leu Thr Leu Leu Thr His Cys Ala Gly
1               5                   10                  15

Ser Trp Ala Gln Ser Gln Leu Thr Gln Pro Pro Ser Ala Ser Gly Thr
            20                  25                  30

Ala Gly Gln Arg Val Thr Ile Ser Cys Ser Gly Ser Ser Ser Asn Ile
        35                  40                  45

Gly Lys Asn Ser Val Asn Trp Tyr Arg Gln Phe Pro Gly Thr Ala Pro
    50                  55                  60

Lys Leu Leu Ile Ser Ser Asn Ser Gln Arg Thr Ser Gly Val Pro Asp
65                  70                  75                  80

Arg Phe Ser Gly Ser Lys Ser Gly Thr Ser Ala Ser Leu Ala Ile Ser
                85                  90                  95

Gly Leu Gln Ser Asp Asp Glu Ala Asp Tyr Tyr Cys Ala Ala Trp Asp
            100                 105                 110

Asp Asn Leu Ser Trp Glu Ile Phe Gly Gly Gly Thr Lys Leu Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Gly Ser
                165                 170                 175

Pro Val Lys Ala Gly Val Glu Thr Thr Lys Pro Ser Lys Gln Ser Asn
            180                 185                 190
```

```
Asn Lys Tyr Ala Ala Ser Ser Tyr Leu Ser Leu Thr Pro Glu Gln Trp
            195                 200                 205

Lys Ser His Arg Ser Tyr Ser Cys Gln Val Thr His Glu Gly Ser Thr
            210                 215                 220

Val Glu Lys Thr Val Ala Pro Thr Glu Cys Ser
225                 230                 235

<210> SEQ ID NO 22
<211> LENGTH: 475
<212> TYPE: PRT
<213> ORGANISM: Artificial Sequence
<220> FEATURE:
<223> OTHER INFORMATION: #40 heavy chain

<400> SEQUENCE: 22

Met Glu Phe Gly Leu Ser Trp Val Phe Leu Val Ala Ile Leu Lys Gly
1               5                   10                  15

Val Gln Cys Glu Val Gln Leu Val Gln Ser Ala Gly Gly Leu Val Gln
            20                  25                  30

Pro Gly Gly Ser Leu Arg Ile Ser Cys Ala Pro Ser Gly Phe Ser Val
            35                  40                  45

Arg Ala Ser Tyr Met Gly Trp Ile Arg Gln Ala Pro Gly Lys Gly Leu
50                  55                  60

Glu Trp Ile Ser Leu Ile Phe Thr Ala Gly Asn Thr Tyr Tyr Ala Asp
65                  70                  75                  80

Ser Val Arg Gly Arg Phe Thr Val Ser Arg Asp Ser Ser Arg Asn Thr
                85                  90                  95

Leu Tyr Phe Gln Met Asn Asn Leu Arg Val Gly Asp Thr Ala Val Tyr
            100                 105                 110

Tyr Cys Ala Arg Leu Asn Trp Ala Gly Tyr Ala Tyr Gly Pro Ala Tyr
            115                 120                 125

Tyr Tyr Gly Leu Asp Val Trp Gly Gln Gly Thr Thr Val Ile Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
            275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320
```

```
Glu Glu Gln Tyr Asn Ser Thr Tyr Arg Val Val Ser Val Leu Thr Val
            325                 330                 335

Leu His Gln Asp Trp Leu Asn Gly Lys Glu Tyr Lys Cys Lys Val Ser
        340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
            405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 23
<211> LENGTH: 239
<212> TYPE: PRT
<213> ORGANISM: Artificial Sequence
<220> FEATURE:
<223> OTHER INFORMATION: #4 light chain

<400> SEQUENCE: 23

Met Arg Leu Pro Ala Gln Leu Leu Gly Leu Leu Met Leu Trp Val Ser
1               5                   10                  15

Gly Ser Ser Gly Asp Ile Val Met Thr Gln Ser Pro Leu Ser Leu Ser
            20                  25                  30

Val Ala Pro Gly Glu Pro Ala Ser Ile Ser Cys Arg Ser Ser Gln Ser
        35                  40                  45

Leu Leu His Ser Lys Gly Tyr Asn Tyr Val Asp Trp Tyr Leu Gln Lys
    50                  55                  60

Pro Gly Gln Ser Pro Gln Leu Leu Ile Tyr Leu Gly Ser Asp Arg Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Ala Leu Gln Ser Pro Val Phe Gly Gly Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205
```

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 24
<211> LENGTH: 473
<212> TYPE: PRT
<213> ORGANISM: Artificial Sequence
<220> FEATURE:
<223> OTHER INFORMATION: #4 heavy chain

<400> SEQUENCE: 24

Met Lys His Leu Trp Phe Phe Leu Leu Leu Val Ala Val Pro Arg Trp
1               5                   10                  15

Val Leu Ser Gln Val Gln Leu Gln Glu Ser Gly Pro Gly Leu Val Arg
            20                  25                  30

Pro Ser Glu Thr Leu Ser Leu Thr Cys Thr Ile Ser Ser Gly Ser Ile
        35                  40                  45

Ser Phe Tyr Tyr Trp Ser Trp Ile Arg Gln Pro Pro Gly Lys Gly Leu
    50                  55                  60

Glu Trp Ile Gly Tyr Val Tyr Ile Ser Gly Asp Thr Asp Tyr Asn Pro
65                  70                  75                  80

Ser Leu Lys Ser Arg Val Thr Ile Ser Val Asp Lys Ser Lys Asn Gln
                85                  90                  95

Phe Ser Leu Lys Leu Arg Ser Val Thr Ala Ala Asp Thr Ala Val Tyr
            100                 105                 110

Tyr Cys Ala Arg Gly His Tyr Gly Ser Gly Ser Asp Tyr Ala Val Tyr
        115                 120                 125

Tyr Phe Asp Arg Trp Gly Gln Gly Ala Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

```
Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
            405                 410                 415

Tyr Lys Thr Thr Pro Pro Val Leu Asp Ser Asp Gly Ser Phe Phe Leu
        420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470
```

EPITOPE OF HEPATITIS B VIRUS SURFACE ANTIGEN AND BINDING MOLECULE SPECIFICALLY BINDING TO SAME FOR NEUTRALIZING HEPATITIS B VIRUS

CROSS-REFERENCE TO RELATED APPLICATIONS

This application is a § 371 national stage of PCT International Application No. PCT/KR2015/012820, filed Nov. 27, 2015, claiming priority of Korean Patent Application No. KR 10-2014-0167937, filed Nov. 28, 2014, the contents of each of which are hereby incorporated by reference into the application.

REFERENCE TO A SEQUENCE LISTING

This application incorporates by reference nucleotide and/or amino acid sequences which are present in the file named "190404_89686_Substitute_Sequence_Listing_BI.txt," which is 21.1 kilobytes in size, and which was created Apr. 3, 2019 in the IBM-PC machine format, having an operating system compatibility with MS-Windows, which is contained in the text file filed Apr. 4, 2019 as part of this application.

TECHNICAL FIELD

The present invention relates to an epitope of hepatitis B virus surface antigen and a hepatitis B virus-neutralizing binding molecule specifically binding thereto.

BACKGROUND ART

Hepatitis B virus (HBV) is DNA virus in the Hepadnaviridae family causing acute and chronic hepatitis, and is regarded as the major cause of liver cirrhosis and liver cancer. HBV is classified into 10 serotypes depending on the response of a hepatitis B virus surface antigen (HBsAg) to standard serum and on the amino acid sequence difference of HBsAg, or into 8 genotypes depending on the gene base sequence difference. There are about 240 million patients with chronic HBV infection worldwide in 2012, and more than half a million people are known to die annually from disease caused by hepatitis B. The chronic HBV infection rate in Korean and Chinese adults is very high, about 5 to 8%, and 80% of adult chronic hepatitis patients, 65% of liver cirrhosis patients, and 70% of patients with hepatocellular carcinoma are associated with HBV infection. Chronic hepatitis B is able to be prevented through the development and spread of vaccines, but is still the most important cause of chronic liver disease, and social expenses due to liver disease are continually increasing. Hence, the development of a new type of antiviral drug able to prevent and treat chronic hepatitis B is urgently required.

Currently useful drugs for the treatment of chronic hepatitis B include interferon (peginterferon), lamivudine, adefovir dipivoxil, entecavir, and tenofovir, and all oral drugs other than interferon are nucleoside/nucleotide analogues. These drugs inhibit the activity of reverse transcriptase of HBV to thus suppress viral DNA replication, ultimately reducing the amount of HBV DNA in the serum, normalizing ALT numbers and ameliorating liver fibrosis.

However, nucleoside analogues cause drug resistance upon long-term use, thus deteriorating drug efficacy, resulting in aggravated hepatitis. In the case of the most recently developed tenofovir, resistance has not yet been reported, but lamivudine, which has been the most widely used worldwide, is known to exhibit a resistance incidence rate of 70 to 80% after 5 years. Furthermore, since these oral drugs do not directly suppress HBV infection, in order to prevent vertical infection from mother to fetus and re-infection in liver transplant patients, a human plasma-derived hepatitis B immune globulin (HBIg) formulation is used together with the oral drug.

Existing HBIg is prepared by separating an antibody from the blood of a person having an antibody against hepatitis B using the advanced purification technique and removing the potential contaminant source using the virus inactivation technique. However, the material plasma is difficult to obtain, thus requiring excessive importation costs and making it impossible to meet the demand. Moreover, although it takes a lot of time and money to remove the plasma-derived virus, the possibility of existence of a potential source of infection remains, and it is inconvenient to administer due to low efficacy, and considerable economic burden may be imposed.

Furthermore, most antibodies formed through the inoculation of conventional hepatitis B vaccines are known to recognize α-determinants that are located at amino acids 124-147 of HBsAg. The α-determinant acts as the major neutralizing epitope of HBV, but certain mutants in the α-determinant that occurred in some patients have been reported to escape the antibodies formed through inoculation of the hepatitis B vaccines. Accordingly, there is a growing need for the development of novel antibodies or vaccines for the prevention and treatment of hepatitis B, which can respond to escape mutants induced by existing vaccines or HBIg.

DISCLOSURE

Technical Problem

The present invention has been made keeping in mind the problems encountered in the related art, and the present inventors have developed an epitope including amino acids at positions 110, 118, 120 and/or 147 of a hepatitis B virus surface antigen (HBsAg), and have also confirmed it to have three-dimensional structural characteristics.

Accordingly, the present invention is intended to provide an epitope of HBsAg.

In addition, the present invention is intended to provide an HBV-neutralizing binding molecule specifically binding to the epitope.

In addition, the present invention is intended to provide a polynucleotide encoding the binding molecule.

In addition, the present invention is intended to provide an expression vector including the polynucleotide.

In addition, the present invention is intended to provide a host cell for producing an HBV-neutralizing binding molecule through transfection with the expression vector.

In addition, the present invention is intended to provide a composition for the prevention, treatment or diagnosis of hepatitis B, including the binding molecule.

In addition, the present invention is intended to provide a polynucleotide encoding the epitope.

In addition, the present invention is intended to provide an expression vector including the polynucleotide encoding the epitope.

In addition, the present invention is intended to provide a recombinant microorganism or virus, which is transformed with the expression vector including the polynucleotide encoding the epitope.

In addition, the present invention is intended to provide a method of producing an epitope, including incubating the recombinant microorganism or virus.

In addition, the present invention is intended to provide an HBV vaccine composition including the epitope or the polynucleotide encoding the epitope.

In addition, the present invention is intended to provide a composition for detecting HBV including the epitope or the polynucleotide encoding the epitope.

Technical Solution

Therefore, in the present invention, an epitope of human antibody specifically binding to HBsAg (see PCT/KR2014/004612, hereinafter referred to as "inventive antibody") has been found to include amino acids at positions 110, 118, 120 and/or 147 of HBsAg. Also, a sequence or a portion thereof, including these four amino acids, is provided in the form of a three-dimensional structure, thereby forming an epitope to which the inventive antibody is able to bind, which thus culminates in the present invention.

Accordingly, the present invention provides an epitope of 3 to 38 mer selected from among amino acids at positions 106 to 151 of HBsAg.

In an embodiment of the present invention, the epitope may include amino acids at positions 110, 118, 120 and/or 147 of HBsAg. The epitope including amino acids at the above positions may be used in the form of being linked with a carrier in order to maintain a three-dimensional structure thereof or to ensure efficiency thereof upon use for a vaccine composition or the like. In the present invention, any carrier may be used so long as it is biocompatible and is suitable for realizing the effects of the present invention, and is preferably selected from among, but is not limited to, a peptide, serum albumin, immunoglobulin, hemocyanin, and polysaccharide.

In an embodiment of the present invention, the epitope may be amino acids at positions 106-110, 107-111, 108-112, 109-113, 110-114, 114-118, 115-119, 119-123, 120-124, 143-147, 144-148, 145-149, 146-150, 147-151, 110-118, 118-120, 116-120, 117-121, 118-122, 120-147, 110-120, 118-147 or 110-147 of HBsAg.

In the present invention, the HBsAg wild-type full amino acid sequence of HBV genotype C (subtype adr) may be represented by SEQ ID NO:1, and the sequence information may also be verified in Genbank No. GQ872210.1.

In addition, the present invention provides an HBV-neutralizing binding molecule specifically binding to an epitope including at least one amino acid residue selected from the group consisting of amino acids at positions 110, 118 and 120 of HBsAg. Also, the epitope may further include an amino acid at position 147 of HBsAg.

In an embodiment of the present invention, the HBV-neutralizing binding molecule specifically binding to the epitope may have a binding affinity of less than $1\times10^{-9}$ M. In another embodiment, the binding molecule may have a binding affinity of less than $9\times10^{-10}$ M. In still another embodiment, the binding molecule may have a binding affinity of less than $8\times10^{-10}$ M. In yet another embodiment, the binding molecule may have a binding affinity of less than $7\times10^{-10}$ M. In still yet another embodiment, the binding molecule may have a binding affinity of less than $6\times10^{-10}$ M. In a further embodiment, the binding molecule may have a binding affinity of less than $5\times10^{-10}$ M. In still a further embodiment, the binding molecule may have a binding affinity of less than $4\times10^{-10}$ M. In yet a further embodiment, the binding molecule may have a binding affinity of less than $3\times10^{-10}$ M. In still yet a further embodiment, the binding molecule may have a binding affinity of less than $2\times10^{-10}$ M. In still another further embodiment, the binding molecule may have a binding affinity of less than $1\times10^{-10}$ M. In yet another further embodiment, the binding molecule may have a binding affinity of less than $1\times10^{-11}$ M. In still yet another further embodiment, the binding molecule may have a binding affinity of less than $1\times10^{-12}$ M.

According to the present invention, the HBV-neutralizing binding molecule may bind to at least one selected from the group consisting of HBsAg subtypes adw, adr, ayw, and ayr, and may thus have neutralizing activity against HBV.

According to the present invention, the binding molecule may bind to HBV genotypes A, B, C, D, E, F, G and H to thus have neutralizing activity.

Also, the binding molecule of the present invention may bind to HBV resistant to lamivudine, adefovir, clevudine or entecavir and may thus have neutralizing activity.

In an embodiment of the present invention, the binding molecule may bind to a mutant antigen at an amino acid position 101, 112, 126, 129, 133, 143, 173, 175, 184, 185 or 196 of HBsAg to thus have neutralizing activity against HBV, but the present invention is not limited thereto.

In an embodiment of the present invention, the mutant antigen may include, but is not limited to, Q101R, K112R, T126N, I126S, Q129H, M133H, P143K, L173F, L175S, A184V, I185M or W196L.

In an embodiment of the present invention, the binding molecule may be an antibody or a fragment thereof. The antibody may include, but is not limited to, a Fab segment, Fv segment, diabody, chimeric antibody, humanized antibody or human antibody. An exemplary embodiment of the present invention provides a complete human antibody binding to HBsAg. Here, the antibody is used in as broad a meaning as possible, and examples thereof may include an intact monoclonal antibody, a polyclonal antibody, a multispecific antibody formed from two or more intact antibodies (e.g. a bispecific antibody), and an antibody fragment that exhibits the desired biological activity. The antibody is a protein that is produced by an immune system able to recognize a specific antigen and bind thereto. In terms of structure, the antibody is typically configured to have a Y-shaped protein composed of four amino acid chains (two heavy chains and two light chains). Each antibody has two domains, that is, a variable domain and an invariable domain. The variable domain, which is located at the ends of the arms of Y, binds to the target antigen and interacts therewith. The variable domain includes a complementarity-determining region (CDR) that recognizes the specific binding site on the specific antigen and binds thereto. The invariable domain, which is located at the tail of Y, is recognized by the immune system and interacts therewith. The target antigen has a plurality of binding sites called epitopes, recognized by CDR on antibodies. Respective antibodies specifically binding to different epitopes have different structures. Therefore, a single antigen may have at least one antibody corresponding thereto.

In an embodiment of the present invention, the binding molecule comprises a polypeptide sequence comprising any one selected from the group consisting of: i) a sequence comprising, as determined according to the Kabat method, a CDR1 region of SEQ ID NO: 5, a CDR2 region of SEQ ID NO: 6 and a CDR3 region of SEQ ID NO: 7; ii) a sequence comprising, as determined according to the Kabat method, a CDR1 region of SEQ ID NO: 8, a CDR2 region of SEQ ID NO: 9 and a CDR3 region of SEQ ID NO: 10; iii) a sequence comprising, as determined according to the Kabat method, a CDR1 region of SEQ ID NO: 11, a CDR2 region of SEQ ID NO: 12 and a CDR3 region of SEQ ID NO: 13; and iv) a sequence comprising, as determined according to the Kabat method, a CDR1 region of SEQ ID NO: 14, a CDR2 region of SEQ ID NO: 15 and a CDR3 region of SEQ ID NO: 16.

In another embodiment of the present invention, the binding molecule comprises a polypeptide sequence comprising, as determined according to the Kabat method, a CDR1 region of SEQ ID NO: 5, a CDR2 region of SEQ ID NO: 6 and a CDR3 region of SEQ ID NO: 7; and a CDR1 region of SEQ ID NO: 8, a CDR2 region of SEQ ID NO: 9 and a CDR3 region of SEQ ID NO: 10.

In another embodiment of the present invention, the binding molecule comprises a polypeptide sequence comprising, as determined according to the Kabat method, a CDR1 region of SEQ ID NO: 11, a CDR2 region of SEQ ID NO: 12 and a CDR3 region of SEQ ID NO: 13; and a CDR1 region of SEQ ID NO: 14, a CDR2 region of SEQ ID NO: 15 and a CDR3 region of SEQ ID NO: 16.

In the present invention, the complementarity determining regions (CDRs) of variable domains were determined using a conventional method according to the system designed by Kabat et al. (see Kabat et al., Sequences of Proteins of Immunological Interest (5th), National Institutes of Health, Bethesda, Md. (1991)). CDR numbering used in the present invention was performed according to the Kabat method, but the present invention also encompasses binding molecules comprising CDRs determined by other methods, including the IMGT method, the Chothia method, and the AbM method.

In another embodiment of the present invention, the binding molecule comprises a polypeptide sequence comprising any one selected from the group consisting of SEQ ID NOS: 17 to 20.

In another embodiment of the present invention, the binding molecule comprises a variable region represented by SEQ ID NO: 17 and a variable region represented by SEQ ID NO: 18.

In still another embodiment of the present invention, the binding molecule comprises a variable region represented by SEQ ID NO: 19 and a variable region represented by SEQ ID NO: 20.

In another embodiment of the present invention, the binding molecule comprises a polypeptide sequence comprising any one selected from the group consisting of SEQ ID NOS: 21 to 24.

In another embodiment of the present invention, the binding molecule comprises a light chain represented by SEQ ID NO: 21 and a heavy chain represented by SEQ ID NO: 22.

In still another embodiment of the present invention, the binding molecule comprises a light chain represented by SEQ ID NO: 23 and a heavy chain represented by SEQ ID NO: 24.

Furthermore, the present invention includes a functional variant of the antibody. The variants of the antibodies are regarded as a functional variant of the inventive antibody, so long as they may compete with the inventive antibody in order to specifically bind to HBV or its surface antigen (HBsAg) subtype. The functional variant includes, but is not limited to, derivatives the primary conformational sequences of which are substantially similar, and examples thereof include in-vitro or in-vivo modifications, chemicals and/or biochemicals, and they are not found in the parent monoclonal antibody of the present invention. Examples of such modifications may include acetylation, acylation, covalent bonding of nucleotides or nucleotide derivatives, covalent bonding of lipids or lipid derivatives, crosslinking, disulfide bonding, glycosylation, hydroxylation, methylation, oxidation, pegylation, proteolysis and phosphorylation. The functional variant may be selectively an antibody having an amino acid sequence resulting from subjecting at least one amino acid to substitution, insertion, deletion or combinations thereof, compared to the amino acid sequence of the parent antibody. Furthermore, the functional variant may include the truncated form of the amino acid sequence in one or both of an amino terminal and a carboxyl terminal. The functional variant of the present invention may have binding affinity the same as or different from or higher or lower than that of the parent antibody of the present invention, but may still bind to HBV or its surface antigen (HBsAg) subtype. For example, the amino acid sequence of the variable domain, including, but not being limited to, a framework structure or a hypervariable domain, especially CDR3, may be modified. Typically, a light- or heavy-chain domain includes three hypervariable domains having three CDRs and more conserved domains, namely a framework region (FR). The hypervariable domain includes an amino acid residue from CDR and an amino acid residue from a hypervariable loop. The functional variant, which falls within the scope of the present invention, may have an amino acid sequence homology of about 50%~99%, about 60%~99%, about 80%~99%, about 90%~99%, about 95%~99%, or about 97%~99% with the parent antibody of the present invention. In order to optimally arrange amino acid sequences to be compared and also in order to define similar or identical amino acid residues, among computer algorithms, Gap or Bestfit, known to those skilled in the art, may be used. The functional variant may be obtained by subjecting the parent antibody or a portion thereof to a known molecular biological process including PCR or mutagenesis/partial mutagenesis using an oligomer nucleotide, or to an organic synthesis process, but the present invention is not limited thereto.

In addition, the present invention provides a polynucleotide encoding the above binding molecule. For example, the present invention includes an isolated nucleic acid molecule encoding the anti-HBsAg monoclonal antibody.

In addition, the present invention provides an expression vector including the above polynucleotide. The expression vector may include, but is not limited to, any one selected from the group consisting of an expression vector available from Celltrion, such as a MarEx vector and a commercially widely useful pCDNA vector, F, R1, RP1, Co1, pBR322, ToL, and Ti vector; a cosmid; phages, such as lambda, lambdoid, M13, Mu, p1 P22, Qμ, T-even, T2, T3, T7, etc.; and plant viruses, and any expression vector known to those skilled in the art may be used in the present invention, and the expression vector may be selected depending on the properties of the target host cell. The introduction of the vector into the host cell may be performed through calcium phosphate transfection, viral infection, DEAE-dextran-mediated transfection, lipofectamine transfection, or electroporation, but the present invention is not limited thereto, and those skilled in the art may adopt an introduction process suitable for the expression vector and the host cell. The expression vector may contain at least one selection marker, but is not limited thereto, and selection is possible depending on whether or not the product is obtained using the vector including no selection marker. The selection marker is selected depending on the target host cell, which is performed using any process known to those skilled in the art, and thus the present invention is not limited thereto. Furthermore, in order to easily purify the nucleic acid molecule of the present invention, a tag sequence may be inserted into the expression vector and thus fused. The tag may include, but is not limited to, a hexa-histidine tag, hemagglutinin tag, myc tag or flag tag, and any tag may be useful in the present invention so long as it facilitates purification as known to those skilled in the art.

Also, in another embodiment of the present invention, the present invention pertains to a host cell for producing the binding molecule having neutralizing activity against HBV through transfection with the expression vector. In the present invention, the host cell may include, but is not limited to, mammals, plants, insects, fungi, or cells of cellular origin. The mammal cells may include, but are not limited to, CHO cells, F2N cells, CSO cells, BHK cells, Bowes melanoma cells, HeLa cells, 911 cells, AT1080 cells, A549 cells, HEK 293 cells or HEK293T cells, and any cells may be used so long as they are useful as host cell for mammals as known to those skilled in the art.

In addition, the present invention provides a composition for the prevention, treatment or diagnosis of hepatitis B, including the above binding molecule. The composition of the present invention may further include, as an antiviral drug, interferon, an anti-HBV monoclonal antibody, an anti-HBV polyclonal antibody, a nucleoside analogue, a DNA polymerase inhibitor, a siRNA preparation or a therapeutic vaccine, in addition to the binding molecule.

According to the present invention, the composition including the binding molecule may be provided in the form of a formulation, such as a sterile injection solution, a lyophilized formulation, a pre-filled syringe solution, an oral formulation, an external medicine or a suppository through respective typical processes, but the present invention is not limited thereto.

Also, in another embodiment of the present invention, the present invention pertains to a method of treating hepatitis B, comprising administering the above composition in a therapeutically effective amount to a subject infected with HBV. In the treatment method of the present invention, a therapeutic agent known to those skilled in the art may be administered therewith. In the treatment method of the present invention, the administration may be performed orally or parenterally. For example, the administration route may be intravenous administration, but is not limited thereto.

In an embodiment of the present invention, the treatment method may further include administering an antiviral drug. The antiviral drug may include, but is not limited to, interferon, a nucleoside/nucleotide analogue, an anti-HBV monoclonal antibody, an anti-HBV polyclonal antibody, a DNA polymerase inhibitor, a siRNA preparation or a therapeutic vaccine. The nucleoside/nucleotide analogue may include, but is not limited to, lamivudine, entecavir, clevudine or adefovir dipivoxil.

Also, in another embodiment of the present invention, the present invention pertains to a method of preventing hepatitis B, comprising administering the above composition in a therapeutically effective amount to a subject. In the prevention method of the present invention, a prophylactic agent known to those skilled in the art may be administered therewith. In the prevention method of the present invention, the administration may be performed in an oral or parenteral manner. For example, the administration route may be intravenous administration, but is not limited thereto.

The composition of the present invention is administered to a mammal including a human, thereby preventing or treating HBV infection and disease caused by the HBV infection. Herein, the amount of the binding molecule (e.g. antibody) that is administered depends on the treatment subject, severity of disease or status, administration rate and doctor's prescription. Useful as the active ingredient, the binding molecule may be administered once or divided into multiple administrations several times per day in a dose of 0.001 to 10 mg/kg (body weight), or 0.005 to 1 mg/kg (body weight) to a mammal through parenteral routes. In some cases, a dose smaller than the aforementioned range may be more suitable, and a larger dose may be applied without causing side effects and may be distributed in small amounts several times in one day.

Also, in another embodiment of the present invention, the present invention pertains to a method of diagnosing infection with HBV of a patient, comprising i) bringing the above composition into contact with a sample; and ii) detecting a reaction of the composition and the sample. In the diagnosis method of the present invention, the binding molecule (e.g. monoclonal antibody) of the present invention may be coupled with a labeling material in order to detect diagnosis, as necessary, which is already known to those skilled in the art.

In the diagnosis method of the present invention, the sample may be, but is not limited to, any one selected from the group consisting of sputum, saliva, blood, sweat, lung cells, mucus of lung tissue, respiratory tissue and spit of a subject, and the sample may be prepared using a process typically known to those skilled in the art.

Also, in another embodiment of the present invention, the present invention pertains to a method of providing information for diagnosing infection with HBV of a patient, comprising i) bringing the above composition into contact with a sample; and ii) detecting a reaction of the composition and the sample.

Also, in another embodiment of the present invention, the present invention pertains to a kit for diagnosing HBV, comprising i) the above composition; and ii) a vessel. In the diagnosis kit of the present invention, the 2) vessel includes a solid carrier. The binding molecule of the present invention may be attached to a solid carrier, and such a solid carrier may be porous or non-porous, or planar or non-planar.

Also, in another embodiment of the present invention, the present invention pertains to a method of detecting the presence of HBV, comprising bringing the composition into contact with a sample derived from a patient.

In addition, the present invention provides a polynucleotide encoding the epitope. The polynucleotide encoding the epitope including the above amino acid position according to the present invention may be used alone in the form of a gene vaccine. Here, the polynucleotide may be used alone without any vector, and may be embedded in a viral or non-viral vector and then transferred into the body. The viral or non-viral vector may be used without limitation so long as it is known to be typically useful in the art to which the present invention belongs. Particularly, examples of the viral vector may include an adenovirus, an adeno-associated virus, a lentivirus, a retrovirus, etc., and the non-viral vector may include a cationic polymer, a nonionic polymer, a liposome, a lipid, a phospholipid, a hydrophilic polymer, a hydrophobic polymer, and at least one combination selected from among them, but the present invention is not limited thereto.

In addition, the present invention provides an expression vector including the polynucleotide encoding the epitope.

In addition, the present invention provides a recombinant microorganism or virus, which is transformed with the expression vector. In an embodiment, the recombinant microorganism or virus may be recombinant *E. coli*, recombinant yeast, or a recombinant bacteriophage.

In an embodiment of the present invention, the present invention provides a method of expressing, on the surface of a microorganism or virus, the epitope including amino acid at positions 110, 118, 120 and/or 147 of HBsAg. Here, a recombinant vector having a sequence encoding an inducible promoter or a signal protein and any microorganism or virus including the recombinant vector may be used. In particular, the appropriate microorganism or virus may include, but is not limited to, recombinant *E. coli*, recombinant yeast, or a recombinant bacteriophage. In order to express the epitope including the above amino acid positions on the surface of the microorganism or virus, a display technique well-known in the art to which the present invention belongs may be utilized. In particular, the expression method of the invention may be performed in a manner in which a polynucleotide sequence encoding the epitope including the above amino acid positions may bind to the sequence encoding a promoter or signal protein that induces expression on the surface of microorganism cells or virus, or in which some of genes encoding a protein that is originally expressed on the surface may be deleted and then a polynucleotide sequence encoding the epitope including the above amino acid positions may be inserted therein, but the present invention is not limited thereto. When using the expression method of the invention, the epitope including the above amino acid positions expressed on the surface of the microorganism or virus may be isolated and purified and may thus be applied to certain purposes of the present invention, and also it is possible to screen and obtain an antibody specifically binding to the epitope including the above amino acid positions in the state of being expressed on the surface.

In addition, the present invention provides a method of producing the epitope, comprising incubating the recombinant microorganism or virus.

In addition, the present invention provides an HBV vaccine composition including the above epitope or a polynucleotide encoding such an epitope. The HBV vaccine composition may further include a pharmaceutically acceptable adjuvant. The adjuvant functions to increase the formation of an antibody when injected into the body, and any adjuvant may be used so long as it is able to achieve the effects of the present invention, and examples thereof may include, but are not limited to, an aluminum salt ($Al(OH)_3$, $AlPO_4$), squalene, sorbitan, polysorbate 80, CpG, liposome, cholesterol, MPL (monophosphoryl lipid A), and GLA (glucopyranosyl lipid A).

In addition, the present invention provides a composition for detecting HBV, including the above epitope, or a polynucleotide encoding such an epitope.

Advantageous Effects

According to the present invention, an epitope of HBsAg does not include major residues in the α-determinant that produces an escape mutant upon the administration of existing vaccine or HBIg, and thus a composition including an antibody binding thereto or a vaccine composition including the above epitope has a very low possibility of undergoing a reduction in efficacy due to the escape mutant. Hence, such an antibody or vaccine composition can be very useful in the prevention and/or treatment of HBV.

BRIEF DESCRIPTION OF DRAWINGS

FIG. 1 shows the mutant structures in which wide-type HBsAg (226 a.a) is divided into three regions, namely amino acid sequences 1~100 (Region 1), 101~160 (Region 2), and 161~226 (Region 3), and in which respective regions are deleted, in order to identify the binding site of the inventive antibody;

FIG. 2 shows the results of measurement of binding intensity of the inventive antibody to wide-type HBsAg and three kinds of mutant HBsAg in which each of Regions 1, 2, 3 is deleted, through ELISA using phages;

FIG. 3 shows the structures of four kinds of mutant HBsAg in which 15 amino acids are sequentially deleted, in order to identify the epitope of the inventive antibody;

FIG. 4 shows the results of measurement of binding intensity of the inventive antibody to four kinds of mutant HBsAg in which the 15 amino acids are sequentially deleted, through ELISA using phages;

FIG. 5 shows the positions of epitopes and disulfide bonds on the HBsAg models;

FIGS. 6*a* and 6*b* show the results of Western blot assay for identifying the characteristics of the epitope of the inventive antibody;

FIG. 7 shows the results of ELISA of reactivity of the inventive antibodies 1, 2 according to an embodiment of the present invention to various mutant antigens of the α-determinant;

FIGS. 8*a* to 8*d* show the results of in-vitro neutralization tests of the inventive antibodies 1, 2 according to an embodiment of the present invention for four HBV genotypes A, B, C, D, in which the amount of intracellular virus is measured from the amount of HBV DNA that is proliferated, using real-time PCR;

FIGS. 9*a* to 9*d* show the results of in-vitro neutralization tests of the inventive antibodies 1, 2 according to an embodiment of the present invention for four HBV genotypes A, B, C, D, in which the amount of virus that was proliferated and excreted extracellularly is measured from the amount of HBsAg using chemiluminescent immunoassay (CLIA);

FIG. 10 shows the results of sandwich ELISA of binding activity of the inventive antibodies 1, 2 to 15 HBV surface antigen serum samples (derived from patients of seven HBV genotypes A, B, C, D, E, F, H); and FIG. 11 shows the results of sandwich ELISA of binding activity of the inventive antibodies 1, 2 to drug (lamivudine, adefovir, clevudine, entecavir)-resistant viruses.

MODE FOR INVENTION

Examples

A better understanding of the present invention may be obtained via the following examples, which are set forth to illustrate, but are not to be construed as limiting the scope of the present invention. The documents cited herein are incorporated by reference into this application.

Example 1: Identification of Binding Site of Inventive Antibody Using Deletion Mutant Antigen In order to verify the binding site of an inventive antibody to HBsAg, wild-type HBsAg and various deletion mutants of HBsAg were prepared and the binding ability thereof was measured through enzyme-linked immunosorbent assay (ELISA) using phages.

Here, testing was performed in two steps. Particularly, HBsAg (226 a.a) was divided into three regions, namely amino acid sequences 1~100, 101~160, and 161~226, and expression vectors of mutants in which respective regions were deleted and of wild types were prepared (FIG. 1) and each protein was expressed on the phage surface and then the binding intensity thereof to the inventive antibody was measured.

Example 1-1. Preparation of Expression Vectors of Wild-Type HBsAg and Three Kinds of Mutant HBsAg In order to express, on the phage surface, wild-type HBsAg and its three divided portions, namely deletion mutant proteins, cloning was performed using a phage expression vector. The detailed testing method was as follows. To clone wild-type HBsAg and mutants having deleted sites, gene amplification was performed therefor through polymerase chain reaction (PCR) using, as a template, an HBV vector including an HBsAg gene base sequence of HBV genotype C (Department of Pharmacology, Konkuk University School of Medicine), followed by treatment with a restriction enzyme Sfi I and then insertion into the phage expression vector treated with the same restriction enzyme. The manufactured plasmid was extracted using a QIAprep Spin Miniprep Kit (QIAGEN, Germany, Cat #27106), and the base sequence of the antibody was ultimately identified through base sequence analysis using the extracted DNA. The names of the completed clones and the HBsAg sites are shown in Table 1 below.

TABLE 1

Clone information for identifying binding site of inventive antibody

| Clone name | Clone description | HBsAg site (amino acid) |
| --- | --- | --- |
| HBsAg full | Wild-type | 1~226 |
| Region 2 + 3 | Amino acids 1~100 deleted | 101~226 |
| Region 1 + 3 | Amino acids 101~160 deleted | 1~100 & 161~226 |
| Region 1 + 2 | Amino acids 161~226 deleted | 1~160 |

In the present Example, the HBsAg wild-type full amino acid sequence of HBV genotype C (subtype adr) is represented by SEQ ID NO:1, and sequence information may be verified in Genbank No. GQ872210.1.

Example 1-2. Evaluation of Binding Intensity of Inventive Antibody to Wild-Type HBsAg and Three Kinds of Mutant HBsAg To perform the binding test to all or some of the cloned HBsAg, each vector was inserted into expression *E. coli* (ER2738, Lucigen, USA, Cat #60522-2) through electroporation, and antibiotic (ampicillin)-resistant *E. coli* selectively began to grow from the next day. After growth for about 10 hr, *E. coli* was infected with the bacteriophage and another kind of antibiotic (kanamycin) was used to selectively grow the infected *E. coli*. To extract the bacteriophage on the next day, *E. coli* was separated using a centrifuge, and the supernatant was treated with polyethylene glycol (PEG) and allowed to stand in an ice bath for 30 min, after which the bacteriophage was separated again using a centrifuge. The separated bacteriophage was lysed, and the supernatant was filtered, thereby extracting a pure bacteriophage having all or some of HBsAg on the surface thereof.

In order to quantitatively evaluate the binding intensity of the inventive antibody to the wild-type and mutant HBsAg exposed to the bacteriophage surface, ELISA was performed. Particularly, an anti-human Fc antibody (Jackson Immunoresearch, USA, Cat #109-006-098) was mixed with a coating buffer (Sigma, USA, Cat # c3041) and a 96-well plate was coated therewith at 4° C. for one day, followed by binding the inventive antibody thereto. Thereafter, the extracted bacteriophage was attached to the inventive antibody and, using an HRP enzyme-conjugated bacteriophage M13 protein antibody (GE healthcare, USA, 27-9421-01) and then 2,2'-azino-bis(3-ethylbenzothiazoline-6-sulphonic acid) (ABTS, KPL, USA, Cat #50-62-00), the amounts of the bacteriophages having the wild-type and mutant HBsAg bound to the inventive antibody were measured. Here, in order to measure the amounts of all the bacteriophages of individual test groups on which HBsAg was expressed on the surface thereof, an anti-HA antibody (Genescript, USA, Cat # A00168-100) was applied on a 96-well plate at 4° C. for one day, the extracted bacteriophage was attached to the antibody, and measurement was performed in the same manner as above.

Figure 2:
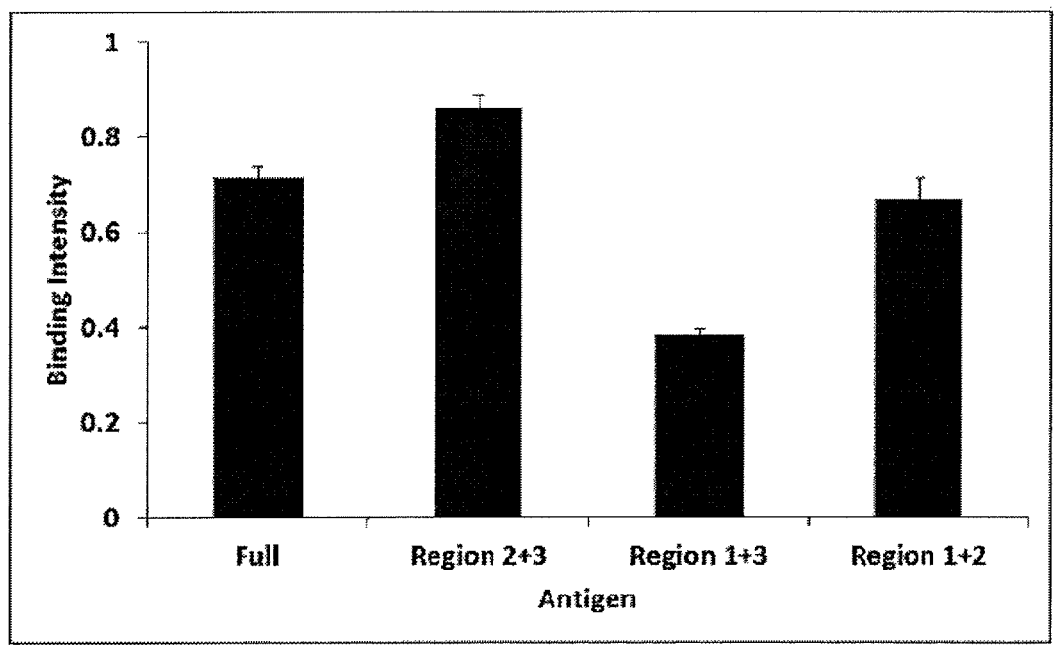

As results thereof, only in the Region 1+3 bacteriophage sample in which HBsAg where amino acid positions 101 to 160 were deleted was expressed on the surface thereof was specifically low binding intensity to the inventive antibody observed (FIG. 2). This means that the major binding site of the inventive antibody was included in Region 2.

Example 2: Identification of Epitope of Inventive Antibody Using Serial-Deletion Mutant Antigen In order to identify the epitope based on the major binding site of the inventive antibody as confirmed in Example 1, serial-deletion mutants, in which 15 amino acids were sequentially deleted from the starting amino acid position 101 of Region 2, were prepared and then exposed to the bacteriophage surface, followed by measuring the binding intensity thereof to the inventive antibody through ELISA.

Figure 3:
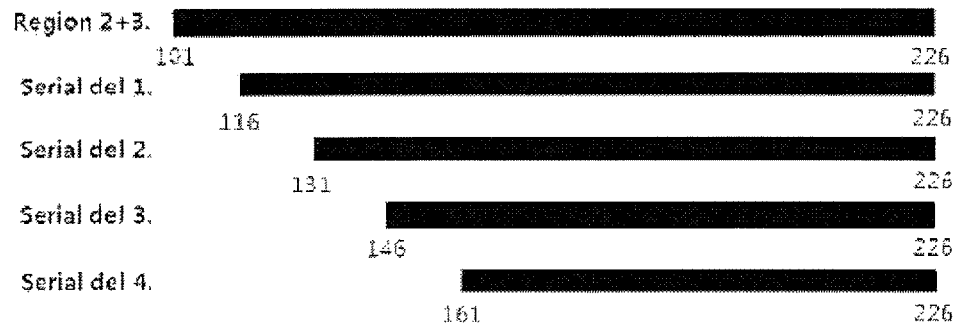

Example 2-1. Preparation of Expression Vectors of Four Kinds of Mutant HBsAg Mutants in which 15 amino acids each were deleted based on Region 2+3 clones were prepared. The names of the completed clones and the HBsAg sites are shown in Table 2 below (FIG. 3). The detailed cloning process overlaps Example 1-1 and thus a description thereof is omitted.

TABLE 2

Clone information for identification of epitope of inventive antibody

| Clone name | Clone description | HBsAg site (amino acid) |
| --- | --- | --- |
| Region 2 + 3 | Amino acid 1~100 deletion | 101~226 |
| Region 2 + 3 Del 1 | Amino acid 1~115 deletion | 116~226 |
| Region 2 + 3 Del 2 | Amino acid 1~130 deletion | 131~226 |
| Region 2 + 3 Del 3 | Amino acid 1~145 deletion | 146~226 |
| Region 2 + 3 Del 4 | Amino acid 1~160 deletion | 161~226 |

Example 2-2. Measurement of Binding Intensity of Inventive Antibody and Four Kinds of Mutant HBsAg ELISA was performed by extracting bacteriophages in which four serial-deletion mutants were exposed to the surface in the same manner as in Example 1-2.

Figure 4:
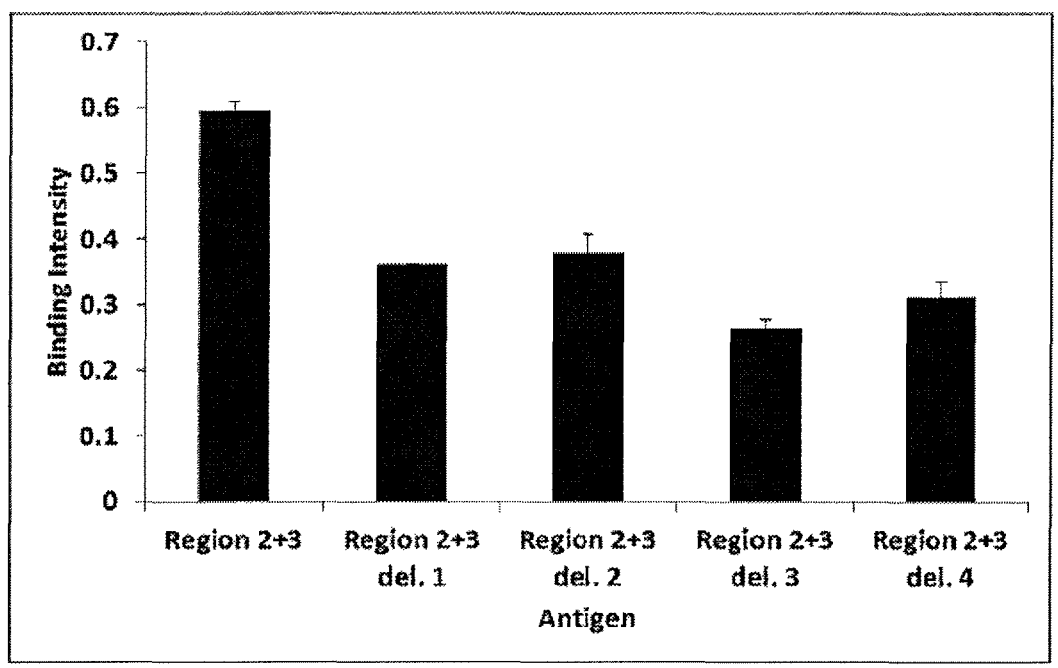

As results thereof, the binding intensity to the inventive antibody was remarkably decreased in Region 2+3 del 1, which means that the major antigenic determinant (epitope) of the inventive antibody is present at amino acid positions 101 to 115 (FIG. 4).

Example 3. Identification of Epitope of Inventive Antibody Using Single Amino Acid Mutant Antigen In order to more accurately identify the epitope of the inventive antibody, random mutagenesis was introduced into HBsAg (subtype adr) using shotgun mutagenesis technology of Integral Molecular, USA (J Am Chem Soc. 2009; 131 (20): 6952~6954), so that the binding ability of the inventive antibody to each mutant antigen was measured. The characteristics of the library of the mutant antigen used for the testing are shown in Table 3 below. Each clone of the library manufactured was expressed in HEK-293T cells incubated on a 384-well plate.

TABLE 3

Characteristics of HBsAg random mutagenesis library used for epitope identification test

| | |
|---|---|
| Total clone number of library | 456 |
| Mutagenized HBsAg residue number (total 226) | 226 (100%) |
| Mutagenized clone number in one residue | 367 |
| Mutagenized clone number in two residues | 78 |
| Mutagenized clone number in three or more residues | 11 |

Example 3-1: Verification of Epitope of Antibody

The binding ability of the inventive antibody to the mutant antigen was measured three times through immunofluorescence FACS, and normalization was implemented based on the reactivity to wild-type HBsAg. Also, the results of binding ability using orb43805, which is a mouse monoclonal antibody against HBsAg, as a control antibody, were employed to confirm the reliability of test results and to set the criteria for epitope selection. Specifically, the mutant residue, present in the clone in which the binding reactivity to the inventive antibody was less than 15% (<15% WT) compared to wild-type HBsAg while the binding reactivity to orb43805 as the control antibody was 55% or more (>55% WT) compared to the binding reactivity to wild-type HBsAg, was selected as the critical residue essential for the binding of the inventive antibody.

Based on the test results, the critical residues for the inventive antibody were derived from a total of four mutant antigens, and thus, the epitope of the inventive antibody was confirmed to have amino acids at positions 110, 118, 120 and 147 of HBsAg. The detailed test results are shown in Table 4 below.

TABLE 4

Critical residues of HBsAg to inventive antibody

| | Binding reactivity (% WT) | |
|---|---|---|
| Mutant | Inventive antibody | orb43805 |
| L110P | 7.9 | 75.7 |
| T118A | 8.3 | 56.3 |
| P120L | 5.7 | 61.4 |
| C147R | 9 | 98.6 |

Among them, the amino acid at position 110 is included in the binding site identified through the testing of Example 2 and thus can be concluded to be a critical epitope for the inventive antibody. The amino acids at positions 118, 120 and 147 are absent in the binding site identified through the testing of Example 2. In the case of deletion testing, however, conformational changes may occur due to the removal of many amino acids, and thus the likelihood that some epitopes may not be identified is high.

Figure 5:
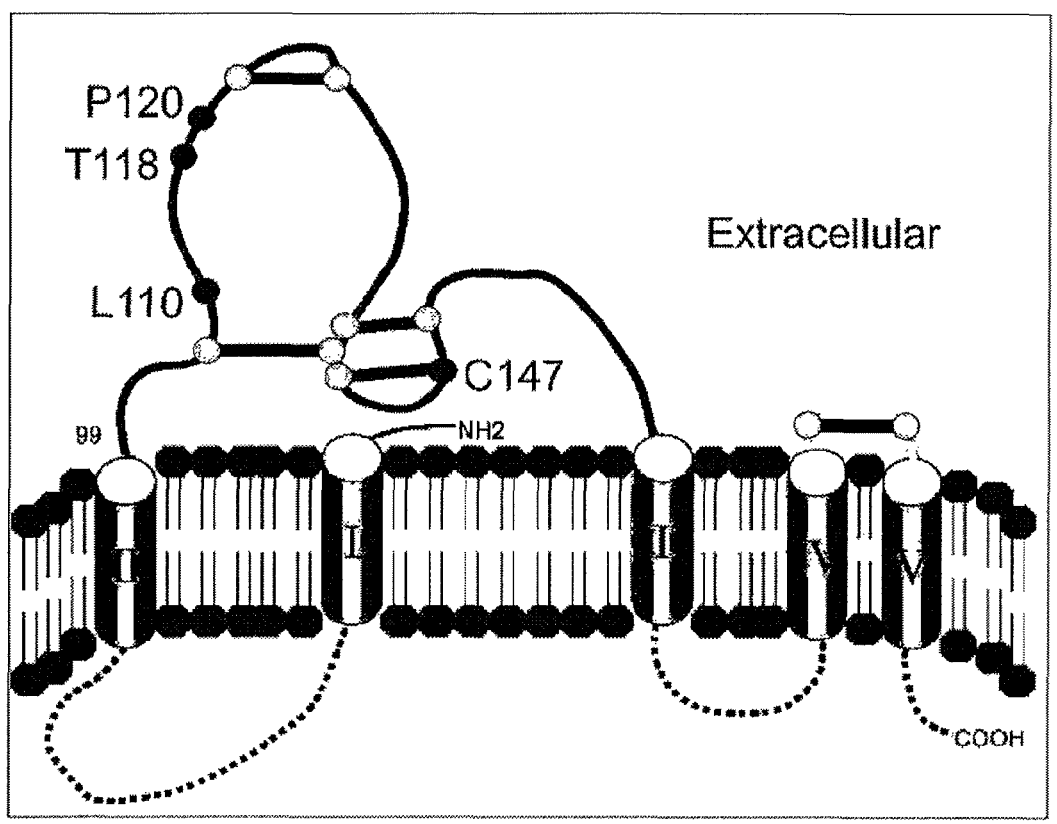

Particularly, HBsAg maintains a three-dimensional structure via disulfide bonds such as C107-C138, C139-C147 and so on. When such bonding is damaged due to the deletion mutant of Example 2, the original structure is broken to thus affect the antibody bonding. In the present Example, the epitope residue, which was not found in the deletion testing of Example 2, was identified through the single mutation testing (FIG. 5). Since the amino acid at position 147 is a residue for forming a disulfide bond important to maintain the three-dimensional structure of HBsAg, it may participate in the binding to the inventive antibody so that the conformational epitope at positions 110, 118 and 120 is normally formed.

Example 4: Identification of Characteristics of Epitope of Inventive Antibody In order to verify whether the conformational epitope is formed from the binding site proven through Examples 1, 2 and 3, Western blot was performed. Here, using both sodium dodecyl sulfate-polyacrylamide gel electrophoresis (SDS-PAGE) gel corresponding to the protein denaturation conditions and Native-PAGE gel corresponding to the non-denaturation conditions, the binding intensity difference of the inventive antibody depending on the structure of HBsAg was measured. In particular, formation of the conformational epitope was observed upon non-linearization and upon linearization by removing a disulfide bond important for forming the tertiary structure of HBsAg, in the presence or absence of the reducing agent under the protein denaturation conditions.

4-1. Western Blot Assay Using Native-PAGE

In order to evaluate whether the inventive antibody was able to recognize the conformational epitope of HBsAg which was naturally formed, Western blot was performed using NativePAGE gel having no SDS. Particularly, a solution containing HBsAg was mixed with a NativePAGE™ Sample Buffer (Invitrogen, USA, Cat # BN2003) and a NativePAGE™ 5% G-250 Sample Additive (Invitrogen, USA, Cat # BN2004), and then loaded on a NativePAGE™ Novex® 3-12% Bis-Tris Protein Gel (Invitrogen, USA, Cat # BN1003BOX). After the gel was run for about 2 hr, the protein of the gel was transferred to a PVDF membrane (Invitrogen, USA, Cat # LC2002) using a NuPAGE® Transfer Buffer (Invitrogen, USA, Cat # NP0006). The membrane was blocked with a phosphate-buffered saline (PBS)-Tween20 buffer including 5% skim milk for 1 hr, after which a primary antibody was added to a PBS-Tween20 buffer including 3% skim milk and the membrane was refrigerated overnight therewith. Here, as a positive control for the inventive antibody, the standard of World Health Organization (WHO) (WHO International Standard for anti-HBs immunoglobulin, human (code: 07/164)) was used, and as a negative control, anti-HER2 antibody, which is a humanized antibody against human epidermal growth receptor2 (HER2), was used. The membrane was sufficiently washed with a PBS-Tween20 buffer, and as a secondary antibody, Horseradish peroxidase (HRP)-conjugated anti-human Fc (Thermo Scientific, USA, Cat #31413) was mixed with a PBS-Tween20 buffer including 3% skim milk and then treated for 1 hr. The membrane was sufficiently washed with a PBS-Tween20 buffer and then treated with an enhanced chemiluminescent (ECL) substrate, after which the binding of HBsAg and each tested antibody was observed using ChemiDoc (BioRad, USA).

Figure 6A:
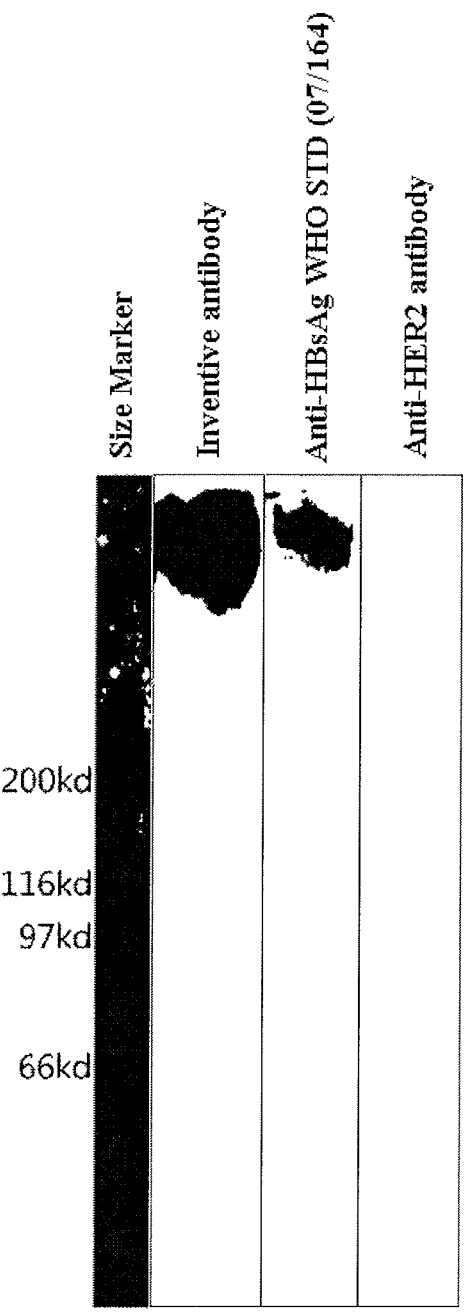
Figure 6B:
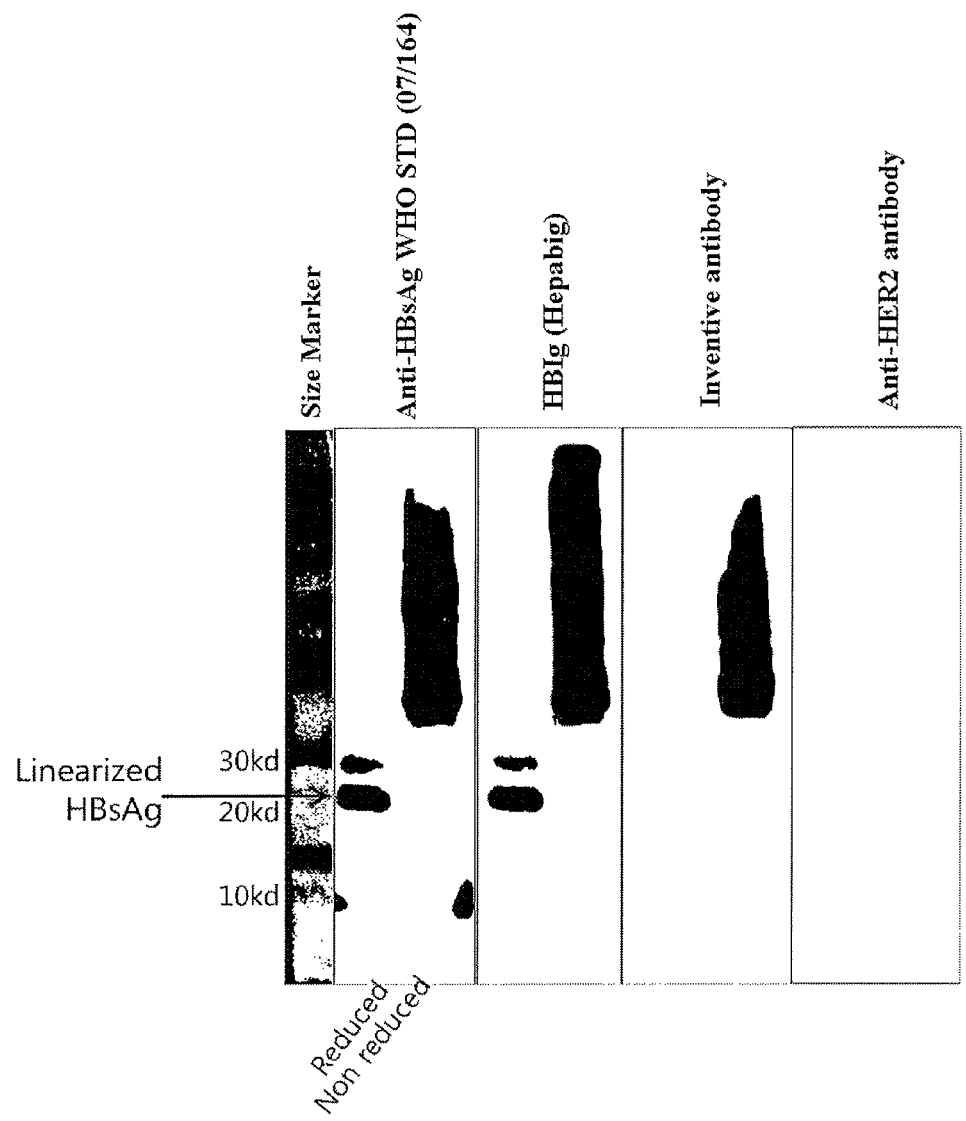

Based on the test results, HBsAg, the natural tertiary structure of which was maintained, exhibited very high binding intensity to the inventive antibody (FIG. 6a). The specificity of this binding was confirmed based on the test results of the WHO standard as the positive control and the anti-HER2 antibody as the negative control. The WHO standard was a polyclonal antibody purified from human blood, and included all antibodies able to recognize the linear and conformational epitopes of HBsAg, and the binding thereof was confirmed in this test, and the anti-HER2 antibody serving as the non-specific antibody was not attached.

Meanwhile, the molecular weight of HBsAg is known to be about 23 kd and the molecular weight of HBsAg bound to the antibody in this test was very large, wherein the formation of native HBsAg in a specific form (a subviral particle having a size of 22 nm) through spontaneous assembly is well known, which can be concluded to be a natural phenomenon (Ira Berkower et al., *J Virol.*, March 2011; 85(5): 2439-2448).

4-2. Western Blot Assay Using SDS-PAGE

In order to more clearly assay the conformational characteristics of the epitope to the inventive antibody, Western blot was performed using SDS-PAGE gel and a reducing agent. The overall test procedures were the same as in Example 4-1, and are briefly described below.

First, an HBsAg solution was mixed with an SDS-PAGE sample buffer, reacted at 95° C. for 5 min, and then loaded on a 4-20% Mini-PROTEAN TGX Precast gel and the gel was run. Here, two kinds of loading samples were prepared, one of which was added with a reducing agent (NuPAGE Sample Reducing Agent (10×), Life Technologies, USA) to thus induce complete protein denaturation, and the other of which did not include a reducing agent to maintain a disulfide bond of HBsAg to thus cause incomplete denaturation. After running, HBsAg was transferred to a nitrocellulose (NC) membrane, blocked, and refrigerated with a primary antibody overnight. Examples of the primary antibody include the inventive antibody, WHO standard, HBIg (Hepabig, Green Cross, Korea), and anti-HER2 antibody. The subsequent procedures were the same as above, and the description thereof is omitted.

As results thereof, the inventive antibody was not attached to the completely linearized HBsAg having no disulfide bond, and was efficiently attached to HBsAg in which partial denaturation occurred. The WHO standard and HBIg serving as the positive controls are polyclonal antibodies as described in Example 4-1, and include the antibody able to recognize a linear epitope and are thus well bound to HBsAg, which is completely linearized under the reducing conditions. The anti-HER2 antibody was not bound regardless of the structure of HBsAg. In the tertiary structure of HBsAg, the importance of the disulfide bond formed in the protein or between proteins is widely known (Mangold C M et al., Arch Virol., 1997; 142(11):2257-67).

Therefore, maintaining the tertiary structure of HBsAg through disulfide bonding is essential for the binding of the inventive antibody, and thus the inventive antibody can be concluded to recognize the conformational epitope of HBsAg.

Example 5: Evaluation of Binding Activity of Inventive Antibody to Various Mutant Antigens of α-Determinant In order to evaluate the binding activity of the inventive antibody to four mutant antigens of the α-determinant, ELISA was performed. These antigens, which were those mutated at amino acid positions 126, 129, 133, and 143, are found in escape mutants induced by vaccines or hepatitis B immune globulin (HBIg) reported in patients with chronic hepatitis B and also cause problems in which the measurement of surface antigen is difficult upon diagnosis (Horvat et al., Lab medicine, vol. 42(8): 488-496, 2011). The recombinant proteins of such antigens were purchased from ProSpec Bio.

Figure 7:
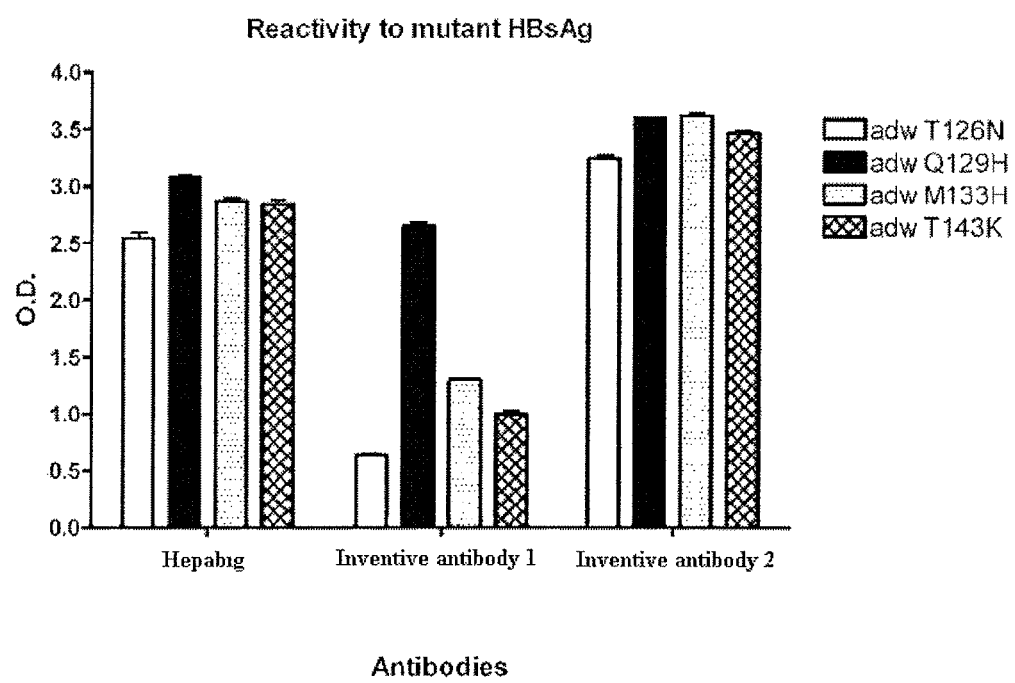
Figure 8A:
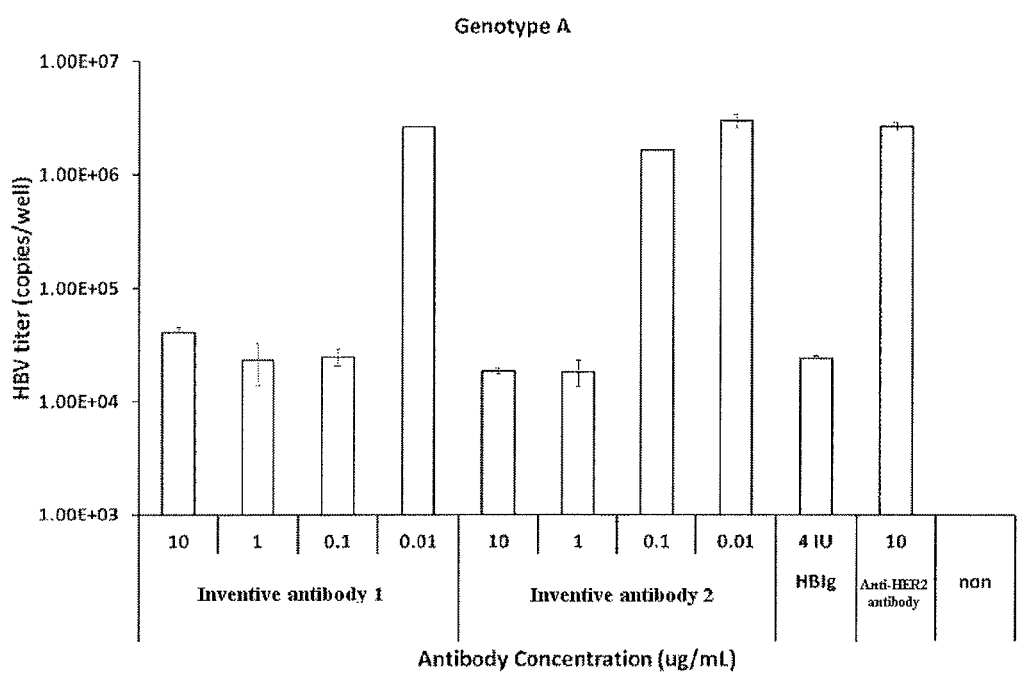
Figure 8B:
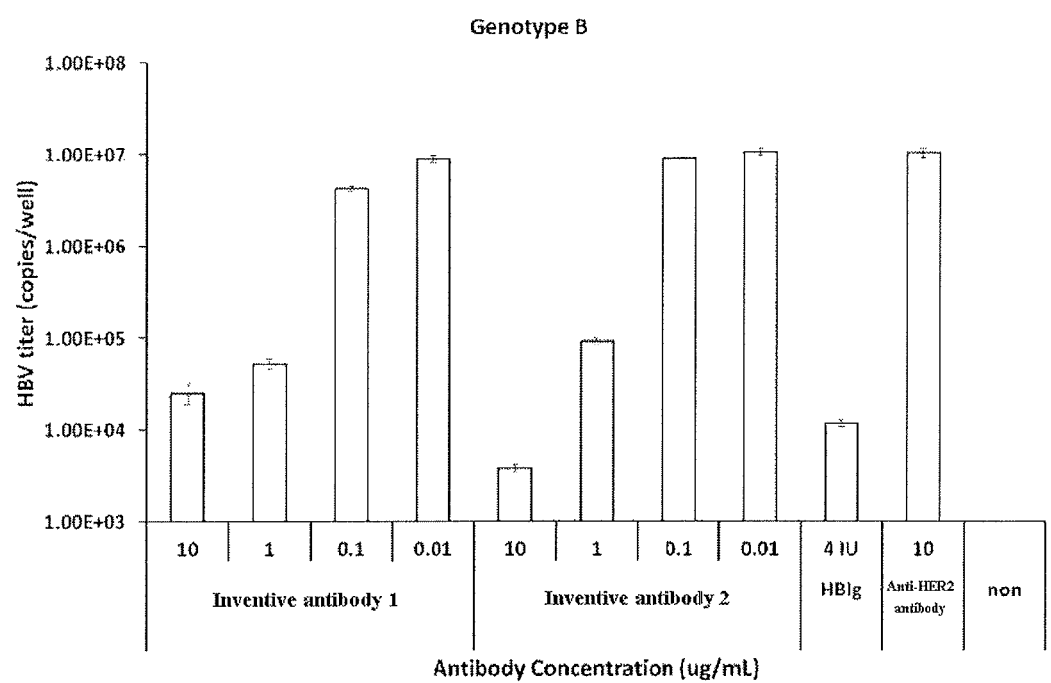
Figure 8C:
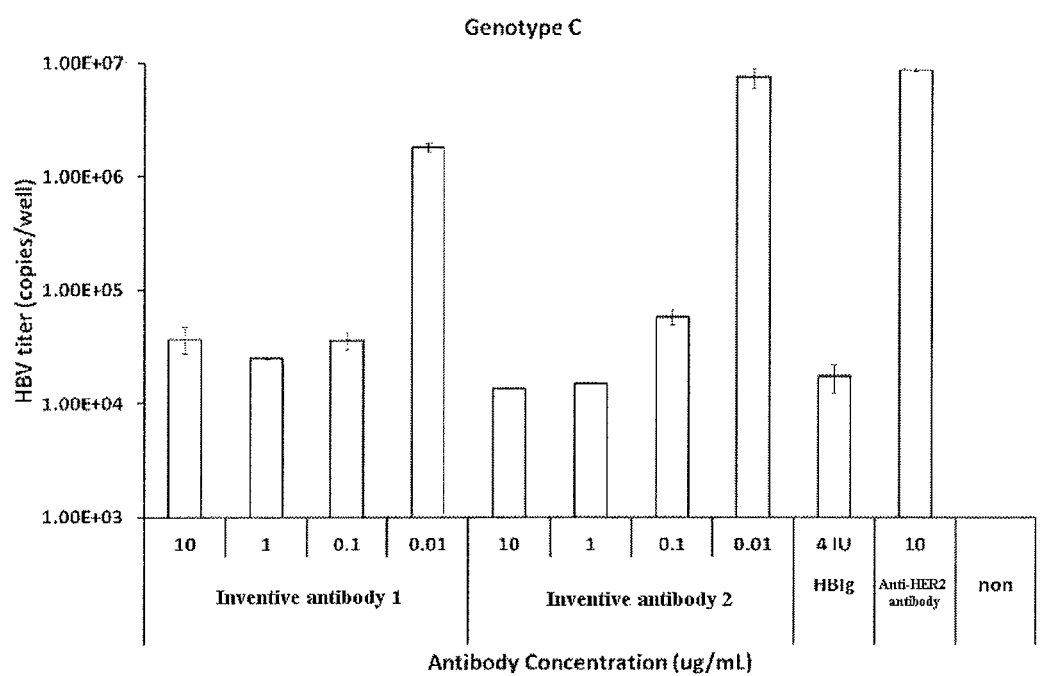
Figure 8D:
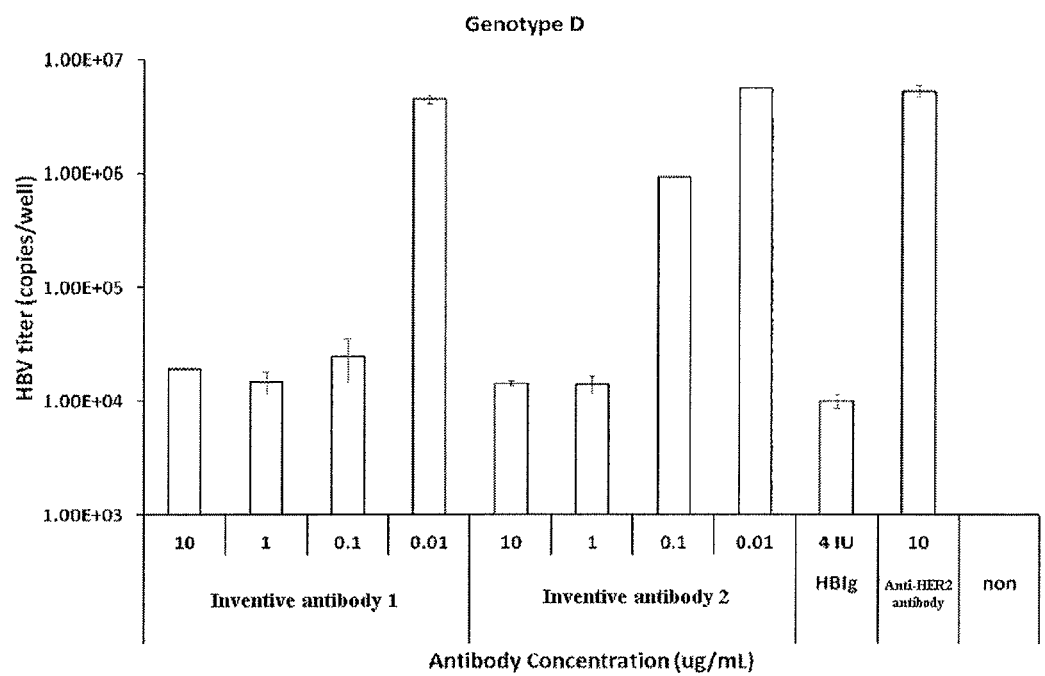
Figure 9A:
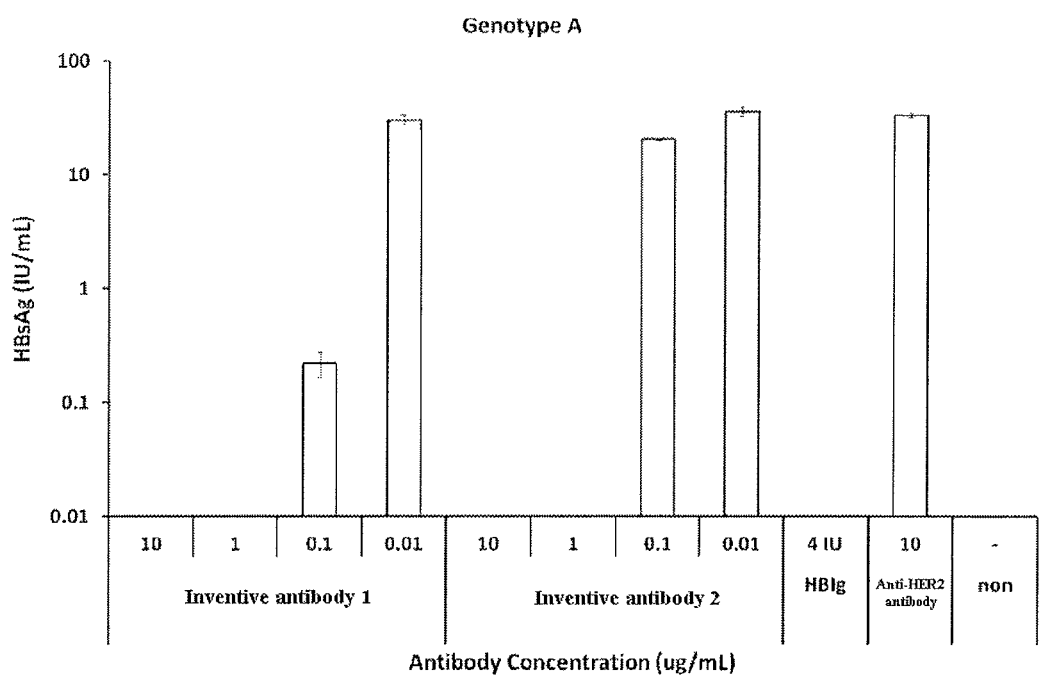
Figure 9B:
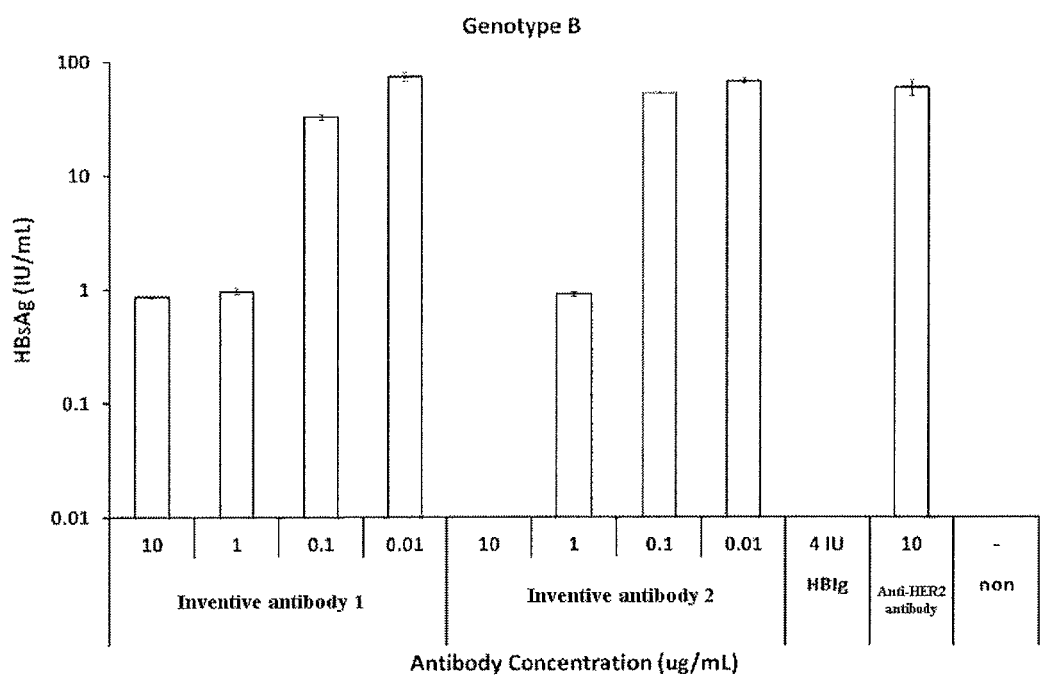
Figure 9C:
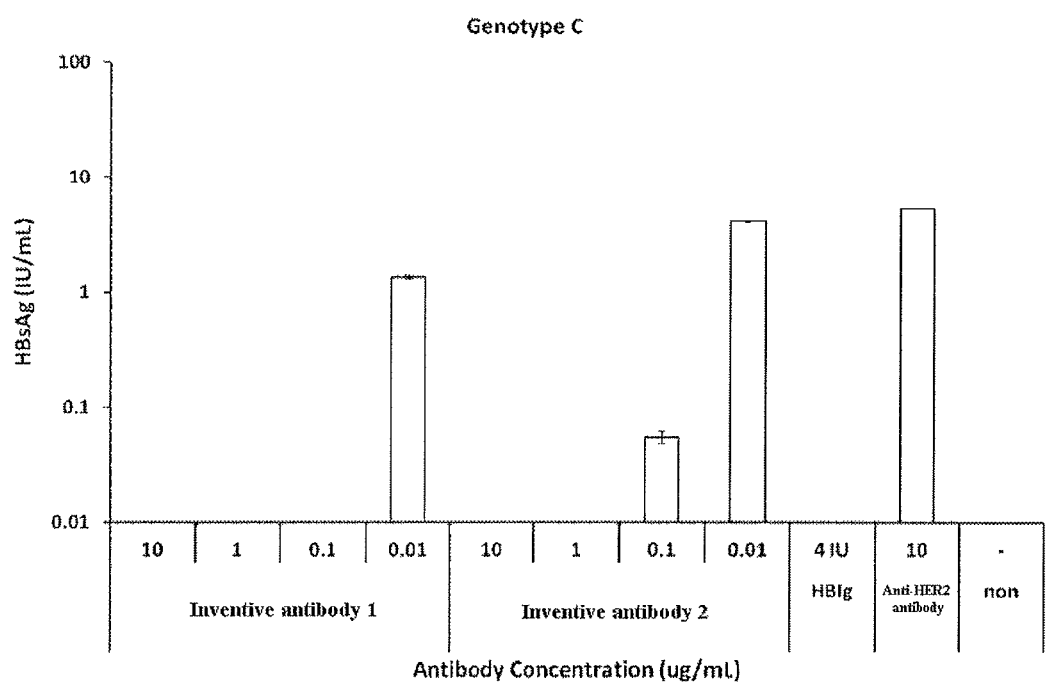
Figure 9D:
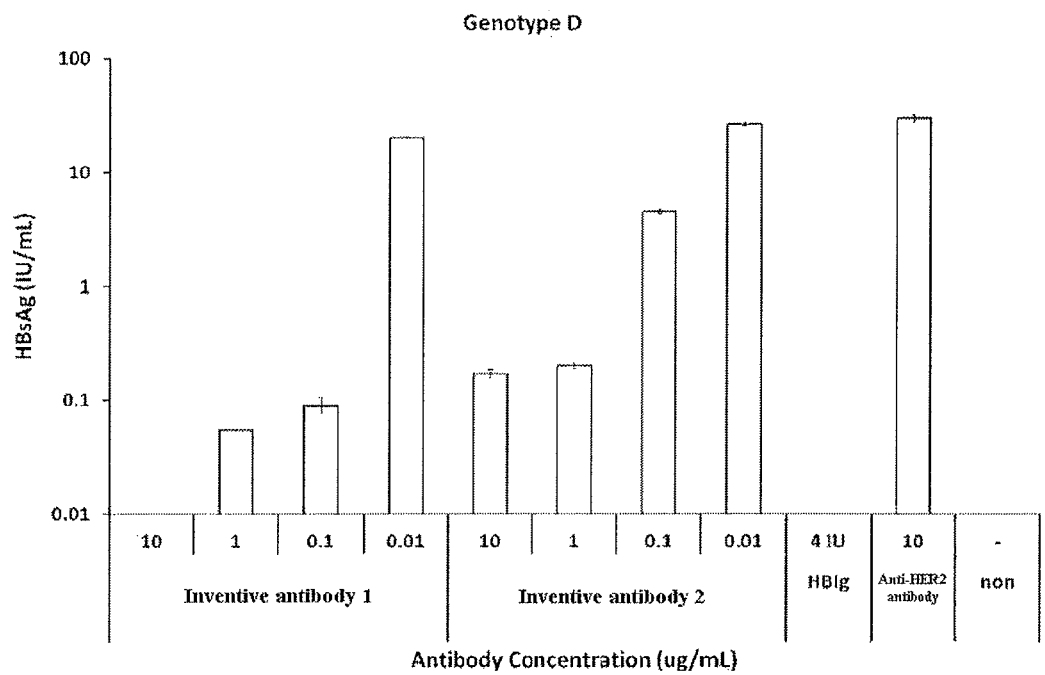

FIG. 7 shows the reactivity of the inventive antibodies 1, 2 to the mutant antigens of the α-determinant, and positive (+) and negative (−) results thereof depending on the presence or absence of the reactivity are summarized in Table 5 below.

TABLE 5

| ELISA results of binding activity of inventive antibody 1, 2 to mutant HBsAg of a-determinant | | |
|---|---|---|
| HBsAg | Inventive antibody 1 | Inventive antibody 2 |
| adw T126N | + | + |
| adw Q129H | + | + |
| adw M133H | + | + |
| adw T143K | + | + |

As test results thereof, the inventive antibody 1, 2 had binding ability to various kinds of mutant HBsAg of the α-determinant. Since the inventive antibody is able to recognize the epitope at positions 110, 118, 120 and/or 147 of HBsAg, it may not be affected by an α-determinant having a high mutation rate (amino acids 124-147).

The amino acid at position 147 is a residue important for forming the conformation, and the mutation of such a residue is known to have a severe influence on infectivity, and thus the actual mutation rate is expected to be very low.

Therefore, the vaccine composition including the epitope at positions 110, 118, 120 and/or 147 or the antibody binding to the above epitope has a low likelihood of decreasing the efficacy due to the escape mutants, and is useful in the prevention or treatment of HBV.

Example 6: Verification of In-Vitro Neutralizing Activity Against HBV

In order to verify the neutralizing activity of the inventive antibody against various genotypes of HBV, an in-vitro neutralization assay was performed.

An in-vitro neutralization test for HBV is a method of evaluating the neutralizing activity of an antibody by measuring the amounts of intracellular and extracellular viruses at the most active stage of viral proliferation, in order to evaluate the extent of inhibiting the infection of human hepatocytes with virus depending on the treatment conditions of each antibody. The amount of intracellular virus was measured from the amount of HBV DNA that was proliferated, and the amount of virus that was proliferated and excreted extracellularly was measured from the amounts of HBsAg and HBV DNA in the medium. Here, an HBV DNA was quantified through real-time PCR using a TaqMan probe and HBsAg was quantified through chemiluminescent immunoassay (CLIA).

6-1. 1st In-Vitro Neutralization Test

Human hepatocytes necessary for infection with HBV were prepared through two-step collagenase perfusion from uPA/SCID chimeric mouse with humanized liver tissue the day before viral inoculation. The separated hepatocytes were applied at a concentration of $4 \times 10^5$ per well on a 24-well plate coated with Type 1 collagen. As the culture medium, 500 µl of DMEM (Gibco, USA, 11965), including 10% FBS (Atlas Biologicals, USA, F0500A), 1x penicillin/streptomycin (Gibco, USA, 15140) and 20 mM HEPES (Gibco, USA, 15630), was used per well. The prepared hepatocytes were incubated in a 5% $CO_2$ humidified cell incubator at 37° C. for 24 hr.

Viral infection was carried out in a manner in which four genotypes of HBV, referred to as A (Genbank accession number: AB246345.1), (Genbank accession number: AB246341), (Genbank accession number: AB246338.1), and D (Genbank accession number: AB246347), each of which was produced from chimeric mice having humanized liver tissue, were mixed with the inventive antibody and then applied at a viral concentration of $2 \times 10^6$ per well. The detailed description thereof is as follows.

A. Preparation of Viral Inoculation Mixture

The virus and each antibody were mixed so that the final volume was 100 µl using a dHCGM medium (DMEM+10% FBS, 44 mM $NaHCO_3$, 15 µg/ml L-proline, 0.25 µg/ml insulin, 50 nM dexamethasone, 5 ng/mM EGF, 0.1 mM Asc-2p, 2% DMSO), and were then reacted at room temperature for 1 hr. Here, the viral concentration was $2 \times 10^6$, and the inventive antibody was diluted at four concentrations of 10, 1, 0.1, and 0.01 µg/ml.

B. Viral Inoculation

125 µl of a dHCGM medium and 25 µl of 40% PEG (Sigma, USA, P1458) were mixed and added with the virus/antibody mixture prepared in A above, thus obtaining 250 µl of the final inoculation mixture. The culture medium was removed from the prepared cells and the inoculation mixture was introduced, followed by incubation for 24 hr.

C. Medium Exchange and Culture, and Preparation of Analytical Sample

After viral inoculation, the hepatocytes were incubated for a total of 12 days, and cell washing and medium exchange were performed on the 1st day, 2nd day, and 7th day. The existing culture medium was removed, washing was performed with 500 µl of DMEM+10% FBS, and the same amount of dHCGM medium was newly placed. As for the medium exchange on the 7th day, the existing culture medium was collected in respective amounts of 300 µl and 30 µl to quantify extracellular HBsAg and HBV DNA excreted from the cells, and stored at −20° C. until analysis.

After the completion of incubation for 12 days, all of the cells and the medium were used for intracellular/extracellular viral quantitative analysis. The culture medium was separately collected for measurement of HBsAg and HBV DNA in the same manner as before, and the cells were collected in a manner in which each well was washed once with 500 µl of DMEM+10% FBS and then lysed with 500 µl of a SMITEST (Medical & Biological Laboratories Co., Ltd.) solution. The extraction of HBV DNA was performed according to the protocol of the manufacturer (Medical & Biological Laboratories Co., Ltd.).

D. Sample Analysis

The quantification of HBV DNA was performed through real-time PCR using a TaqMan probe, TaqMan PCR Core Reagents (Life Technologies, USA), and an ABI Prism 7500 sequence detector system (Applied Biosystems, USA). Also, HBsAg was quantified through ARCHITECT (Abbott, USA) as a CLIA-aided automatic system.

TABLE 6

Primer/probe sequence for real-time PCR for HBV quantification

| Primer/Probe | Sequence | SEQ ID NO: |
|---|---|---|
| Forward primer | CACATCAGGATTCCTAGGACC | 2 |
| Reverse primer | AGGTTGGTGAGTGATTGGAG | 3 |
| TaqMan probe | CAGAGTCTAGACTCGTGGTGGACT-TC (Dye: FAM for 5', TAMRA for 3') | 4 |

TABLE 7

Real-time PCR program

| Program | Cycle |
|---|---|
| 50° C. 2 min | 1 |
| 95° C. 10 min | 1 |
| 95° C. 20 sec → 60° C. 1 min | 53 |
| Threshold | 0.1 |

The test results for the inventive antibodies 1, 2 are shown in FIGS. 8a to 8d and 9a to 9d depending on the virus genotype in each measurement item.

The amounts of intracellular HBV DNA depending on the treatment concentration of each antibody were compared and analyzed. Particularly, the inventive antibodies 1, 2, which were chosen based on the binding intensity to HBsAg subtype adr of genotype C, can be found to have strong neutralizing activity against genotype C. In the state in which the amount of HBV DNA was decreased by at least 400 times in HBIg serving as the positive control compared to the anti-HER2 antibody serving as the negative control, the same level of viral DNA reduction was also exhibited in the sample treated with 1 µg/ml inventive antibody 2, corresponding to 1/10 of the treatment amount thereof. As for the inventive antibody 1, the amount of HBV DNA was decreased by 100 times even at a low treatment concentration of 0.1 µg/ml, thus maintaining relatively high neutralizing activity. Furthermore, the neutralizing activity of the inventive antibodies 1, 2 against genotypes A and B was more than twice as high as the maximum neutralizing activity compared to when HBIg was used as the positive control, and the neutralizing activity against genotype D was maintained high even at a low concentration of 0.1 µg/ml (inventive antibody 1) or 1 µg/ml (inventive antibody 2) (FIGS. 8a to 8d).

The neutralizing activity of the inventive antibodies 1, 2 against four genotypes A, B, C and D was found to be very similar to the quantitative results of extracellular HBsAg measured in the culture medium (FIGS. 9a to 9d).

Conclusively, based on the results of measurement of in-vitro neutralizing activity against four genotypes A, B, C, and D of HBV, the inventive antibodies 1, 2 manifested high neutralizing activity against all the viruses used.

Example 7: Measurement of Binding Characteristics to Various Virus Surface Antigen Genotypes Derived from Chronic Hepatitis B Patients In order to evaluate whether the inventive antibodies 1, 2 may exhibit neutralizing activity through binding to various virus genotypes prevailing worldwide in real-world applications, sandwich ELISA was performed using a reference panel of World Health Organization (WHO) (1$^{st}$ WHO International Reference Panel for HBV Genotypes for HBsAg Assays, PEI code 6100/09) comprising various virus surface antigen genotypes derived from patient sera. The detailed information on the corresponding standard is shown in Table 8 below, and the testing method is as follows.

Figure 10:
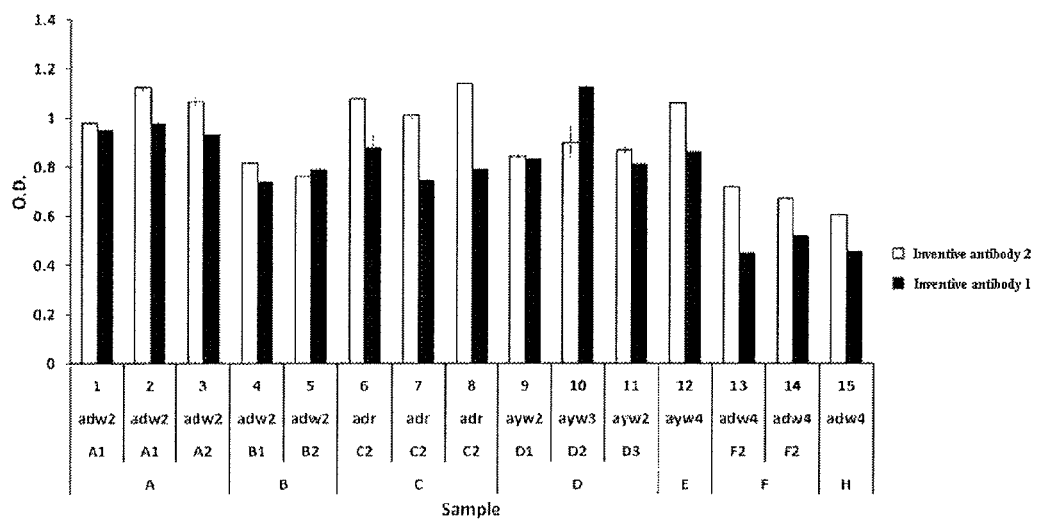

Two antibodies having a concentration of 2 µg/ml were aliquoted in amounts of 100 µl to each well of a 96-well microtiter plate (Nunc, Denmark, 449824) coated with anti-human IgG Fcγ (gamma) antibody (Jackson ImmunoResearch, U.S.A, 109-006-098) and then adsorbed thereto. After washing, the plate was treated with phosphate-buffered saline (Teknova, USA, D5120) containing 3% bovine serum albumin (BSA) and thus blocked. After washing again, 15 serum samples of the HBsAg genotype panel were aliquoted in amounts of 100 µl each and incubated at 37° C. for 90 min. Here, each serum sample was appropriately diluted with phosphate-buffered saline (Teknova, USA, D5120) containing 1% BSA so as to have an absorbance of about 0.8 to 1.2 at 450/620 nm. To detect HBsAg attached to the antibody, peroxidase-labeled rabbit anti-HBV surface antigen antibody (Thermo Scientific, U.S.A., PA1-73087) was treated at 37° C. for 60 min. Color development, reaction termination, and absorbance measurement were performed in the same manner as in Example 5. The reactivity of two antibodies to each HBV surface antigen genotype was graphed and analyzed using Excel (Microsoft, U.S.A.) (FIG. 10).

Based on the analytical results, both of the inventive antibodies 1, 2 were efficiently bound to 15 HBsAg samples. As described above, such surface antigen samples were sera actually prepared from patient blood, and covered seven genotypes A to H excluding genotype G, among a total of eight HBV genotypes. Also, the genotypes A, B, C, D, and F having various sub-genotypes include two to three samples of sub-genotypes and subtypes (serotypes) that were predominant for each genotype, which means that the HBV genotype panel of WHO used for the testing substantially represents most HBV genotypes prevalent around the world. The panel does not include genotype G, but genotype G has no sub-genotype that has been reported to date and is characterized as subtype (serotype) adw2, and thus the binding activity of the inventive antibodies 1, 2 to genotype G is predictable based on the test results of the five adw2 samples included in the panel.

Therefore, the inventive antibodies 1, 2 exhibited superior binding activity to all 15 samples, which means that these two antibodies are able to bind to all HBV genotypes worldwide to thus manifest the corresponding neutralizing activity.

TABLE 8

Detailed information of patient-derived serum HBV surface antigen panel (1$^{st}$ WHO International Reference Panel for HBV genotypes for HBsAg assays, PEI code 6100/09)

| Sample # | Origin | Genotype | sub-genotype | Subtype |
|---|---|---|---|---|
| 1 | South Africa | A | A1 | adw2 |
| 2 | Brazil | | A1 | adw2 |
| 3 | Germany | | A2 | adw2 |
| 4 | Japan | B | B1 | adw2 |
| 5 | Japan | | B2 | adw2 |
| 6 | Japan | C | C2 | adr |
| 7 | Japan | | C2 | adr |
| 8 | Russia | | C2 | adr |
| 9 | Germany | D | D1 | ayw2 |
| 10 | Russia | | D2 | ayw3 |
| 11 | South Africa | | D3 | ayw2 |
| 12 | West Africa | E | N/A | ayw4 |
| 13 | Brazil | F | F2 | adw4 |
| 14 | Brazil | | F2 | adw4 |
| 15 | Germany | H | N/A | adw4 |

Example 8: Evaluation of Binding Characteristics to Various Drug-Resistant Viruses The binding characteristics between the inventive antibodies 1, 2 and mutants resistant to HBV polymerase inhibitors widely useful for chronic hepatitis B patients, for example, lamivudine (LMV), adefovir (ADV), clevudine (CLV), and entecavir (ETV), were measured using the same sandwich ELISA as in Example 7. All resistant mutant viruses including the wild-type virus used in the testing were those cloned in the Department of Pharmacology, Konkuk University School of Medicine, using HBV DNA obtained from the blood of patients having resistance to the corresponding drug treatment, and are stains, the drug resistance of which was experimentally confirmed through transduction using a Huh7 cell line or a HepG2 cell line (Ahn et al., Journal of Virology, 88(12): 6805-6818, 2014). All viruses are genotype C, and the features of individual viruses are shown in Table 9 below.

Each HBV expression vector thus prepared was transduced into the Huh7 cell line grown in a T75 flask (BD BioScience, 353136) using Lipofectamine2000 (Life technologies, 11698019), and incubated for 3 days to thus produce viruses. The produced viruses were concentrated using Centricon (Millipore, U.S.A.), and the viral amount of each sample was compared with the amount of HBsAg using a Monolisa HBsAg Ultra (BioRad, 72346) ELISA kit and then appropriately diluted so as to have similar values and thus used for testing.

Figure 11:
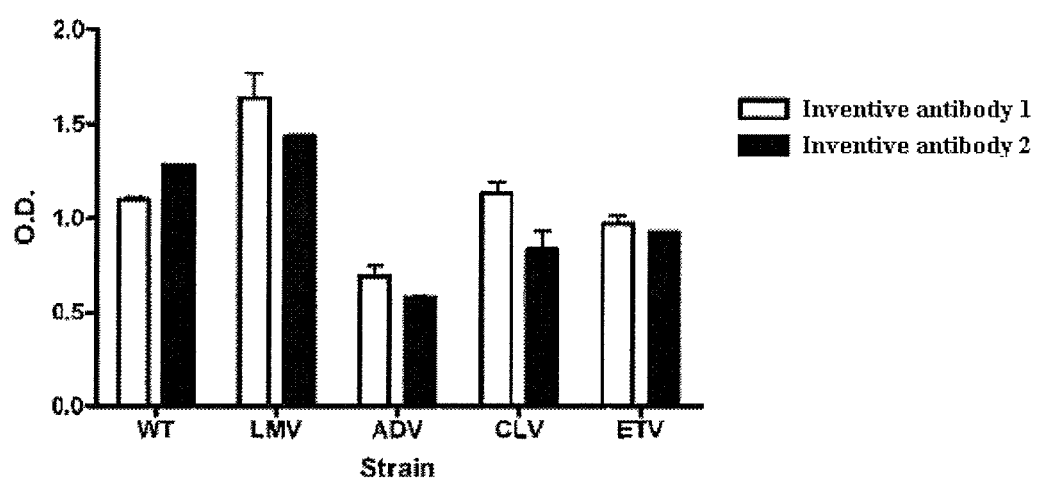

Based on the test results, both of the inventive antibodies 1, 2 were shown to have binding activity to lamivudine (LMV)-, adefovir (ADV)-, clevudine (CLV)-, and entecavir (ETV)-resistant viruses at the same level as in the wild-type virus (FIG. 11). Here, binding activity to ADV-resistant virus appears to be relatively low, which is but deemed to be because the production of the corresponding sample itself is slightly lower than those of the other samples.

This means that the inventive antibodies 1, 2 are able to have binding activity and neutralizing activity not only to one kind of drug-resistant virus used for the test but also to most viruses resistant to the corresponding drugs. This is because the mutation that causes drug resistance to HBV is associated with the specific amino acid mutation of the reverse transcriptase (RT) domain of the HBV polymerase, as shown in Table 9, and such mutation occurs very specifically for each drug. Such specific polymerase mutation includes the specific mutation of HBsAg based on the characteristics of gene-sharing HBV. For example, rtM204I mutation of polymerase results in W196L mutation of HBsAg, and rtA181V mutation results in L173F mutation of HBsAg. The inventive antibodies 1, 2 can be found to be efficiently bound regardless of the surface antigen mutation resulting from the drug resistance mutation.

Furthermore, individual resistant viruses used in this test have many surface antigen mutations that non-specifically occurred, in addition to the aforementioned resistance-specific surface antigen mutations (Table 9). This result shows that the inventive antibodies 1, 2 have the binding and neutralizing activities to viruses in which the Q101R, K112R, I126S, L175S, A184V, I185M positions of HBsAg are mutated.

TABLE 9

Drug-resistant virus information used for test

| Strain | Mutation position of HBV polymerase (RT domain) | Mutation position of HBsAg |
|---|---|---|
| Wild type (genotype C) | N/A | N/A |
| LMV-resistant virus | L80I, M204I | W196L |
| ADV-resistant virus | A181V | I126S, L173F, L175S |
| CLV-resistant virus | M204I | Q101R, I126S, A184V, W196L |
| ETV-resistant virus | L180M, M204V | Q101R, K112R, I185M |

Example 9: Measurement of Antigen-Antibody Binding Affinity

In order to measure the antigen-antibody binding affinity of the inventive antibody, surface plasmon resonance (SPR) was performed. Particularly, the binding affinity of recombinant HBsAg (subtype adr, ProSpec Bio) and the inventive antibody was determined through SPR analysis by means of a Biacore T200 (GE Healthcare) using an analytical buffer HBS-EP (10 mM HEPES [pH 7.4], 150 mM NaCl, 3 mM EDTA and 0.005% surfactant P20) at 25° C. 50 μg/ml HBsAg protein diluted in 10 mM sodium acetate (pH 5.0) was directly fixed by about 500 RU to a biosensor chip for CMS research using an amine coupling kit according to the protocol and procedure of the manufacturer. The portion not reacted on the surface of the biosensor was blocked with ethanolamine. For reaction analysis, Biacore T200 control software and Biacore T200 evaluation software were used. The inventive antibody was diluted in an HBS-EP buffer. During the testing, the biosensor surface having no fixed-HBsAg was used as a control in all measurements. The association and dissociation rate constants Ka (M-1s-1) and Kd (s-1) were determined at a flow rate of 30 μl/min. The rate constant was obtained with 3-fold serial dilutions by measuring the reaction binding at an antibody concentration of 2.46 to 200 nM and using the buffer as a control. Subsequently, the equilibrium dissociation constant KD(M) for the reaction between the antibody and the target antigen was calculated from the reaction rate constant using the following Equation: KD=Kd/Ka. The binding was recorded by calculating as a function of time and the reaction rate constant.

The test results are shown in Table 10 below, from which the high binding affinity of the inventive antibody to HBsAg was confirmed.

TABLE 10

Measurement of binding affinity using recombinant HBsAg

| Sample | ka1(1/Ms) | kd1(1/s) | KD | AVR KD |
|---|---|---|---|---|
| Inventive antibody | 9.04E+04 | 6.33E−05 | 7.00E−10 | 7.45E−10 |
| | 8.12E+04 | 6.42E−05 | 7.90E−10 | |

The invention claimed is:

1. A binding molecule for neutralizing hepatitis B virus (HBV), which specifically binds to an epitope that includes the amino acids at positions 110, 118 and 120 of a hepatitis B virus surface antigen (HBsAg), the amino acid sequence of which antigen is set forth in SEQ ID NO:1, wherein the binding molecule is a human monoclonal antibody or a fragment of such an antibody which comprises a polypeptide sequence comprising the CDR regions of SEQ ID NOS: 5 to 10 or the CDR regions of SEQ ID NOS: 11 to 16.

2. The binding molecule of claim 1, wherein the epitope further includes an amino acid at position 147.

3. The binding molecule of claim 1, wherein the binding molecule has a binding affinity of less than $1 \times 10^{-9}$ M.

* * * * *